(12) United States Patent
Gimzewski et al.

(10) Patent No.: US 8,524,488 B2
(45) Date of Patent: Sep. 3, 2013

(54) METHODS AND DEVICES FOR DETERMINING A CELL CHARACTERISTIC, AND APPLICATIONS EMPLOYING THE SAME

(75) Inventors: James K. Gimzewski, Santa Monica, CA (US); Andrew E. Pelling, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 707 days.

(21) Appl. No.: 11/077,266

(22) Filed: Mar. 9, 2005

(65) Prior Publication Data

US 2005/0239047 A1 Oct. 27, 2005

Related U.S. Application Data

(63) Continuation-in-part of application No. PCT/US03/28066, filed on Sep. 8, 2003.

(60) Provisional application No. 60/410,015, filed on Sep. 10, 2002, provisional application No. 60/562,888, filed on Apr. 15, 2004.

(51) Int. Cl.
*C12M 1/34* (2006.01)

(52) U.S. Cl.
USPC ........... 435/287.9; 435/4; 435/7.2; 435/29; 435/287.1; 435/288.7; 359/838; 359/850; 359/855; 359/884

(58) Field of Classification Search
USPC .................................. 435/4, 7.2, 29
See application file for complete search history.

(56) References Cited

U.S. PATENT DOCUMENTS

| | | | | |
|---|---|---|---|---|
| 4,811,326 | A * | 3/1989 | Gerber | 369/100 |
| 5,232,834 | A * | 8/1993 | Okabe et al. | 435/7.21 |
| 5,912,181 | A * | 6/1999 | Petcavich | 436/151 |
| 6,289,717 | B1 * | 9/2001 | Thundat et al. | 73/23.2 |
| 6,298,715 | B1 * | 10/2001 | Thomson et al. | 73/105 |
| 6,458,547 | B1 * | 10/2002 | Bryan et al. | 506/9 |
| 2003/0058520 | A1 * | 3/2003 | Yu et al. | 359/291 |
| 2004/0142409 | A1 * | 7/2004 | Allen et al. | 435/29 |

OTHER PUBLICATIONS

Whitmarsh, AJ et al. Biological activity of recombinant human ZP3 produced in vitro: potential for a sperm function test. Molecular Human Reproduction. 1996. 2(12): 911-919.*
Domke et al. (1999) *Eur. Biophys. J.* 28:179.186.
Domke et al. (2000) *Colloids and Surfaces B:Biointerfaces* 19:367-379.
Zhang et al. (2001) *Nature* 413:428-432.
A-Hassan et al. (1998) *Biophys. J.* 74:1564-1578.
Rotsch et al. (1997) *Cell Biol. Int.* 21:685-696.
Binnig et al. (1986) *Phys. Rev. Lett* 56:939-933.
Charras et al. (2002) *Biophys. J.* 82:2970-2981.

* cited by examiner

*Primary Examiner* — Allison Ford
*Assistant Examiner* — Susan E Fernandez
(74) *Attorney, Agent, or Firm* — Paula A. Borden; Bozicevic, Field & Francis LLP.

(57) ABSTRACT

The present invention provides methods of determining a characteristic of a cell, such as cell type, cellular response to a biochemical event, and biological state. The method generally involves detecting membrane movement in a cell to determine a characteristic of a cell. The methods of the invention are useful for applications such as drug screening and diagnostics. The invention further provides databases of cell characteristics, as determined by the instant methods. The invention further provides systems for determining the characteristic of a cell.

16 Claims, 11 Drawing Sheets

METHODS AND DEVICES FOR DETERMINING A CELL CHARACTERISTIC, AND APPLICATIONS EMPLOYING THE SAME

CROSS-REFERENCE

This application is a continuation-in-part application of International Patent Application Serial No. US2003/28066, filed Sep. 8, 2003, which was published in English as WO 05/003290 on Jan. 13, 2005, and claims the benefit of U.S. Provisional Patent Application Ser. No. 60/410,015, filed Sep. 10, 2002; and this application claims the benefit of U.S. Provisional Patent Application Ser. No. 60/562,888, filed Apr. 15, 2004; and each of the aforementioned applications is incorporated herein by reference in its entirety.

FIELD OF THE INVENTION

The present invention is in the field of cellular physiology and cell membranes.

BACKGROUND OF THE INVENTION

The cell is one of the oldest nanomachines capable of independent life. Multicellular organisms are communities of cells where each member is capable of responding to its environment but also communicating change to surrounding members of the same community. Cellular systems are complex and carry out a multitude of functions in response to the environment and that directly affect the cellular environment. For example, cells are capable of many complex functions such as motility, cell-cell communication, synthesis of chemicals and macromolecules, and reproduction.

The cell membrane or the cell wall is a fluid and dynamic structure through which all drugs, biochemicals, ions, and cellular signals must pass. Cell membranes are flexible and can assume many different morphologies, depending on cell type and function.

Cellular nanomechanics have been a recent area of study ushered in with the advent of the Atomic Force Microscope (AFM). Force-Volume Imaging, Nano-indentation and Force Spectroscopy have all yielded information regarding the mechanical stability and integrity of cellular membranes in response to normal physiological conditions as well as to stress. However, the currently available methods provide information only about movement of a whole cell, or about the mechanical properties of a cell.

There is a need in the art for methods of determining a characteristic of a cell (e.g., determining the physiological status or biological state of a cell; determining the cell type of a cell; determining the response of a cell to a biochemical event; etc.). The instant invention addresses this need by providing methods of detecting movement of a membrane in a cell, as a readout for the biological state of a cell.

Literature

Domke et al. (1999) *Eur. Biophys. J.* 28:179-186; Domke et al. (2000) *Colloids and Surfaces B:Biointerfaces* 19:367-379; Zhang et al. (2001) *Nature* 413:428-432; A-Hassan et al. (1998) *Biophys. J.* 74:1564-1578; Rotsch et al. (1997) *Cell Biol. Int.* 21:685-696; Binnig et al. (1986) *Phys. Rev. Lett* 56:939-933; Charras et al. (2002) *Biophys. J.* 82:2970-2981.

SUMMARY OF THE INVENTION

The present invention provides methods of determining a characteristic of a cell, such as cell type, cellular response to a biochemical event, and biological state. The method generally involves detecting membrane movement in a cell to determine a characteristic of a cell. The methods of the invention are useful for applications such as drug screening and diagnostics. The invention further provides databases of cell characteristics, as determined by the instant methods. The invention further provides systems for determining the characteristic of a cell.

Features of the Invention

The present invention features a micromirror (e.g., a quantum nanomirror) comprising a reflector surface and a cell attachment surface, wherein the surface area of the micromirror is in a range of from about 25 $nm^2$ to about 75 $\mu m^2$. In some embodiments, the reflector surface comprises a diffraction grating. In some embodiments, the cell attachment surface of the micromirror comprises a cell attachment moiety immobilized on the cell attachment surface. Cell moieties include, e.g., an antibody, a polypeptide, an integrin, a virus attachment protein, a carbohydrate, and a ligand for a cell surface receptor. The present invention also features an array of a subject micromirror, e.g., an array comprising a plurality of subject micromirrors. In some embodiments, the array is a two-dimensional array.

The present invention also features a method for determining a cell characteristic. The method generally comprises detecting a movement of a membrane of the cell to determine a characteristic of a cell, e.g., a living cell. Cell characteristics include, e.g., a response to a stimulus, a cell type, and a biological state of the cell. In some embodiments, the biological state is uncontrolled cell division, such as occurs in a cancerous cell. In some embodiments, the cell membrane in which movement is detected is a membrane of a single cell. In other embodiments, the membrane is a membrane of a subcellular organelle. In other embodiments, the membrane is a membrane of a cell in a tissue. In other embodiments, the membrane is a membrane of a cell in a colony of cells. In some embodiments, the cell is a eukaryotic cell.

In some embodiments, a subject method for determining a cell characteristic comprises directing an incident beam of light on the cell, wherein the cell comprises a subject micromirror positioned on the cell surface; and detecting a beam of light reflected from the micromirror, to detect a movement of the membrane of the cell. In some embodiments, the membrane movement is in response to an external stimulus. In some of these embodiments, the cell is in a liquid medium, and wherein the external, stimulus is delivered into the liquid medium. In other embodiments, the membrane movement is in response to an internal stimulus.

In some embodiments, a subject method for determining a cell characteristic comprises directing an incident beam of light on each cell of a plurality of cells, wherein each cell comprises a subject micromirror positioned on the cell surface; and detecting a beam of light reflected from each micromirror.

In some embodiments, a subject method for determining a cell characteristic comprises contacting the cell with a cantilever probe of an atomic force microscope; and detecting movement of the probe to detect a movement of the membrane of the cell. In some embodiments, the movement of the probe is vertical movement. In other embodiments, the movement of the probe is lateral movement. In some embodiments, the probe has a radius in the range of from about 5 to about 50 nm. In some embodiments, the membrane movement is in response to an external stimulus. In some of these embodiments, the cell is in a liquid medium, and wherein the external stimulus is delivered into the liquid medium. In other embodiments, the external stimulus is delivered by the probe. In other embodiments, the membrane movement is in response to an internal stimulus.

In some embodiments, a subject method for determining a cell characteristic provides for detecting membrane movement in a plurality of cells and the method comprises contacting each cell of a plurality of cells with a probe of an atomic force microscope (AFM) in an array of AFM; and detecting movement of the probes. In some of these embodiments, the array is a two-dimensional array. In other embodiments, the array is a three-dimensional array. In some embodiments, the method further comprises transmitting a signal resulting from membrane movement of a first cell in the plurality of cells in response to a stimulus to a second cell in the plurality of cells; and detecting movement of a membrane in the second cell in response to the transmitted signal.

The present invention further features a database comprising a plurality of cell characteristic profiles recorded on a computer readable medium, each of said cell characteristic profiles comprising cell membrane movement data and at least one additional cell parameter. Additional cell parameters include, e.g., a cell type, a biological state, a cell environment, and a stimulus.

The present invention further features a method of identifying an agent that affects a biological activity of a cell, the method generally involving contacting a cell with a test agent, and determining the effect, if any, of the agent on the biological activity of the cell, wherein the determining comprises detecting cell membrane movement.

The present invention further features a method of identifying a characteristic of a test cell, the method generally involving: determining a cell characteristic profile of the test cell to generate a test profile, wherein the cell characteristic profile comprises cell membrane movement data and at least one additional cell parameter; and comparing the test profile with a reference profile in the database of claim 16, wherein said comparing identifies a reference profile that is substantially identical to the test profile, and wherein the reference profile identifies the cell characteristic. In some embodiments, the reference profile indicates that the test cell is abnormal. In some embodiments, the test cell is a cell in a tissue biopsy.

The present invention further features a method for screening for the presence of an analyte in a sample, the method generally involving: contacting a cell with a test sample suspected of containing an analyte; and determining the effect, if any, of the test sample on the cell membrane movement of the cell.

BRIEF DESCRIPTION OF THE DRAWINGS

FIG. 2A depicts a system with a two-dimensional array of cantilevers an a microfluidics device. FIG. 2B depicts a system with multiple probes in contact with a single cell.

FIG. 6A: BY4741 cell; FIG. 6B: W303.1B cells; and FIG. 6C: CC304.1 cells.

FIG. 7A: BY4741 with an applied force of $89.51 \pm 2.50$ nN; FIG. 7B: W303.1B with an applied force of $63.66 \pm 2.59$ nN; and FIG. 7C: CC304.1 with an applied force of $58.49 \pm 2.56$ nN. (Note that the FFT plots are plotted on a linear scale).

DEFINITIONS

Figure 1:
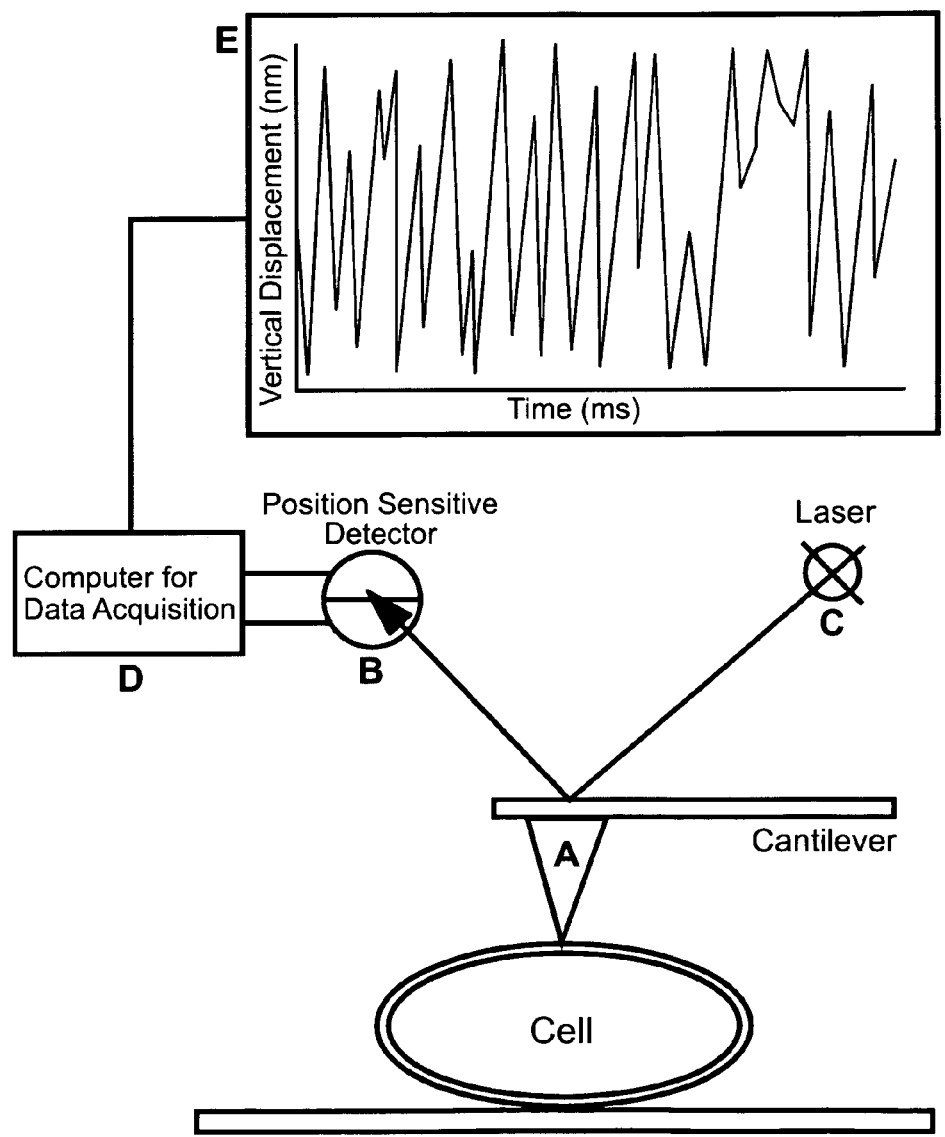
FIG. 1 depicts an example of detecting movement of a membrane of a cell.

As used herein, the term "membrane" refers to a barrier between the cytoplasm of a cell and the extracellular environment, or between the interior of a subcellular organelle and the cytoplasm of a cell. A "membrane" includes a eukaryotic animal, fungal, or yeast cell membrane or cell wall, which generally comprises a lipid bilayer and may include other components such as polypeptides, glycoproteins, lipoproteins, and polysaccharides; a plant cell wall, which generally comprises cellulose, and other components such as lignin, pectins, and hemi-celluloses; a bacterial cell wall (including cell walls of archaebacteria and eubacteria); and the like. Membranes include naturally-occurring membranes, and artificial membranes.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides or polypeptides. The term "biological sample" encompasses a clinical sample, and also includes cells in culture, cell supernatants, cell lysates, serum, plasma, biological fluid, and tissue samples.

The terms "cancer," "neoplasm," and "tumor" are used interchangeably herein to refer to cells which exhibit relatively autonomous growth, so that they exhibit an aberrant growth phenotype characterized by a significant loss of control of cell proliferation. Cancerous cells can be benign or malignant.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a membrane" includes a plurality of such membranes and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of determining a characteristic of a cell, such as cell type, cellular response to a biochemical event, and biological state. The methods generally involve detecting membrane movement in a cell. The methods of the invention are useful for applications such as drug screening and diagnostics. The invention further provides databases of cell characteristics, as determined by the instant methods. The invention further provides systems for determining the characteristic of a cell.

Methods for Determining a Characteristic of a Cell

The instant invention provides methods of determining a characteristic of a cell, typically a living cell. The method generally involves detecting movement of a cell membrane, and relating the movement to a cell characteristic.

Membrane movement is detected using a system that includes at least a membrane movement responsive element; and a detection element for detecting a signal generated by the responsive element. The system may further include a data storage means for storing the signal; and a data processing means, for converting the signal to various formats, for comparing the signal to other stored signals, etc.

Membrane movement is detected by contacting the membrane with an element that responds to membrane movement. The element provides a detectable signal in response to membrane movement. The signal is transmitted or detected by a detection element. The signal detected by the detection element is transmitted to a data processing and storage means, e.g. a computer system. The system may also include an element for transmitting a signal to a cell membrane. Membrane movement includes, but is not limited to, lateral movement, stretching, contracting, and the like.

In some embodiments, the element that responds to membrane movement is a cantilever probe (or tip) of an atomic force microscope (AFM), and the detection element is a photodetector that detects deflection of a laser beam projected onto the cantilever. AFM is described in more detail below.

Figure 2A:
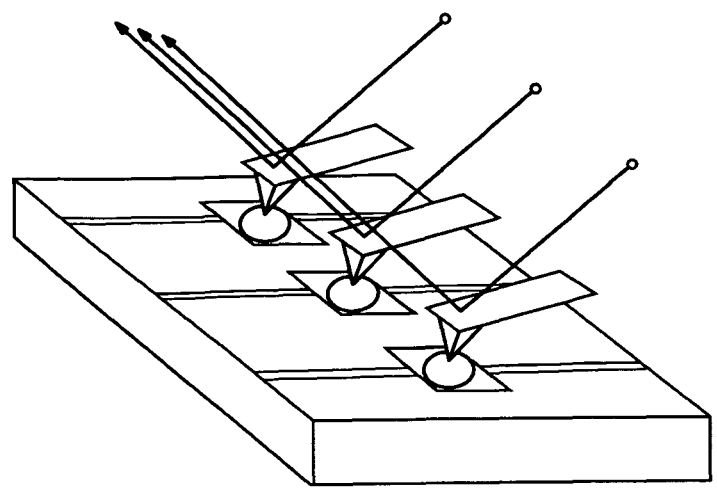
FIGS. 2A and 2B depict various embodiments of the invention.
Figure 2B:
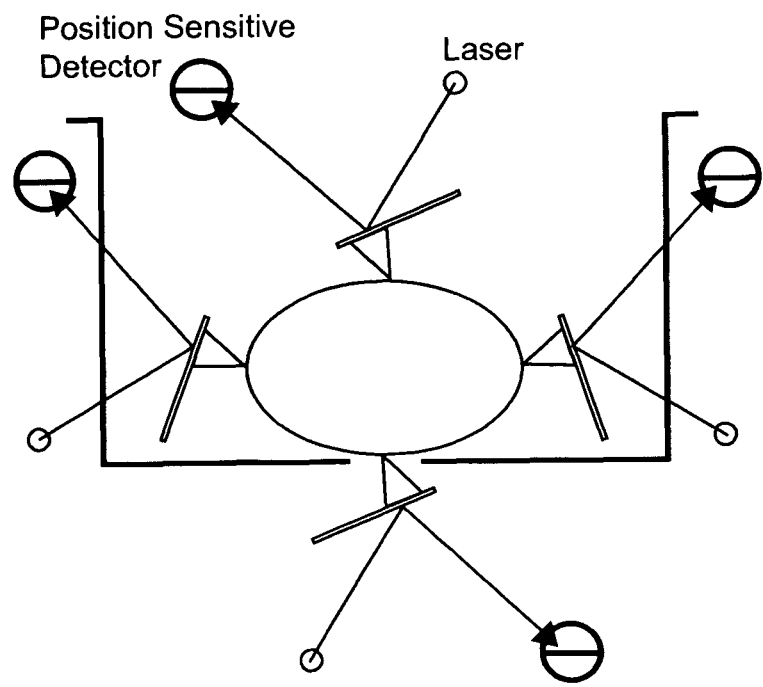
Figure 3:
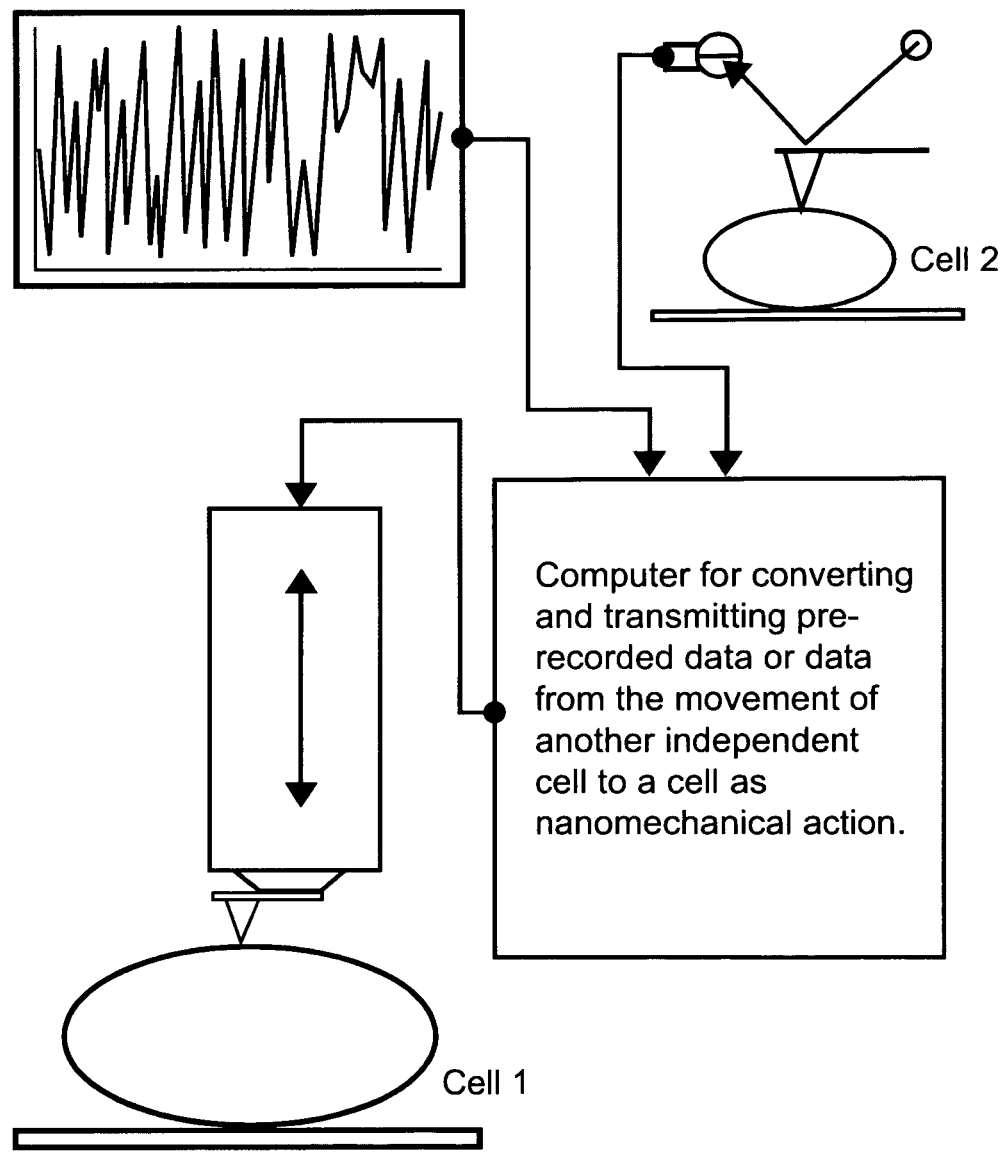
FIG. 3 depicts an embodiment of the invention in which pre-recorded data are transmitted to a cell, or in which data obtained from the membrane movement of a first cell is converted into a signal which is transmitted to a second cell.

Various systems for detecting cell membrane movement are shown in FIGS. 1-3. FIG. 1 depicts an example of detecting movement of a membrane of a cell. FIGS. 2A and 2B depict various embodiments of the invention. FIG. 2A depicts a system with a two-dimensional array of cantilevers on a microfluidics device. FIG. 2B depicts a system with multiple probes in contact with a single cell. FIG. 3 depicts an embodiment of the invention in which pre-recorded data are transmitted to a cell, or in which data obtained from the membrane movement of a first cell is converted into a signal which is transmitted to a second cell.

In other embodiments, membrane movement is analyzed by detecting movement of a mirror attached to the surface of the cell. Movement of the mirror is detected by recording the position of light reflected from the mirror. FIGS. 8-11 depict various systems for detecting cell membrane movement with the use of mirrors attached to the cell surface.

Membrane movement is detected in cells (including naturally-occurring cells and artificial cells) and subcellular organelles. Cells include eukaryotic cells; prokaryotic cells; and artificial cells. Cells include cells in vitro and in vivo, e.g., isolated cells in vitro; cells in colonies in vitro; cells in tissues in vitro; single cells in vivo; cells in tissues in vivo; unicellular organisms; cells of multicellular organisms; and the like. Eukaryotic cells include mammalian cells, reptilian cells, amphibian cells, yeast cells, plant cells, protozoan cells, algae, and the like. Subcellular organelles include the nucleus, mitochondria, Golgi apparatus, vacuoles, and the like. Prokaryotic cells include bacterial cells (e.g., eubacteria), and archaebacterial cells.

As used herein, the term, "cell characteristic" includes: (1) the biological state of a cell; (2) the cell type of a cell; (3) a cell's response to a biochemical event. Membrane movement of the cell is a reproducible read-out for a cell characteristic.

"Biological state" (or "physiological status") includes, but is not limited to, controlled cell division (e.g., mitosis); apoptosis; uncontrolled cell division (e.g., cancerous state); active protein synthesis; quiescence; adhesion to a surface; metastasis; and the like. In general, the cell membrane movement is a reproducible characteristic of the biological state of a cell.

"Cell type" refers to the role that a cell plays under normal physiological conditions. In some embodiments, the amplitude spectrum is characteristic of a cell type. Non-limiting examples of cells are cells of multicellular organisms, e.g., cells of invertebrates and vertebrates, such as myoblasts, neutrophils, erythrocytes, osteoblasts, chondrocytes, basophils, eosinophils, adipocytes, invertebrate neurons (e.g., Helix aspera), vertebrate neurons, mammalian neurons, adrenomedullary cells, melanocytes, epithelial cells, and endothelial cells; tumor cells of all types (e.g., melanoma, myeloid leukemia, carcinomas of the lung, breast, ovaries, colon, kidney, prostate, pancreas and testes); cardiomyocytes, endothelial cells, lymphocytes (T-cell and B cell), mast cells, vascular intimal cells, hepatocytes, leukocytes including mononuclear leukocytes; stem cells such as hematopoietic stem cells, neural, skin, lung, kidney, liver and myocyte stem cells; osteoclasts, connective tissue cells, keratinocytes, melanocytes, hepatocytes, and kidney cells. Suitable cells also include known cell lines, including, but not limited to, Jurkat T cells, NIH3T3 cells, CHO, COS, etc. Cell lines include those found in ATCC Cell Lines and Hybridomas (8$^{th}$ ed, 1994, or latest edition, or on the world wide web at www.atcc.org), Bacteria and Bacteriophages (19$^{th}$ ed., 1996), Yeast (1995), Mycology and Botany (19$^{th}$ ed., 1996), and Protists: Algae and Protozoa (18$^{th}$ ed., 1993), available from American Type Culture Co. (Manassas, Va.). In certain embodiments, muscle cells are specifically excluded, e.g., the cell is not a muscle cell. In certain embodiments, transformed eukaryotic cell lines, such as HEK293 cells, are specifically excluded.

Biochemical events include internal stimuli; external stimuli; gene expression; and the like. In some embodiments, the FFT amplitude spectrum is characteristic of a response of a given cell to an internal or external signal. Movement of the membrane is detected in response to a change in physiological conditions in the cell or organelle. Changes in physiological status are generally in response to an internal or an external signal. External and internal signals (stimuli) include, but are not limited to, infection of a cell by a microorganism, including, but not limited to, a bacterium (e.g., *Mycobacterium* spp., *Shigella, Chlamydia*, and the like), a protozoan (e.g., *Trypanosoma* spp., *Plasmodium* spp., *Toxoplasma* spp., and the like), a fungus, a yeast (e.g., *Candida* spp.), or a virus (including viruses that infect mammalian cells, such as human immunodeficiency virus, foot and mouth disease virus, Epstein-Barr virus, and the like; viruses that infect plant cells; etc.); change in pH of the medium in which a cell is maintained or a change in internal pH; excessive heat relative to the normal range for the cell or the multicellular organism; excessive cold relative to the normal range for the cell or the multicellular organism; an effector molecule such as a hormone, a cytokine, a chemokine, a neurotransmitter; an ingested or applied drug; a ligand for a cell-surface receptor; a ligand for a receptor that exists internally in a cell, e.g., a nuclear receptor; hypoxia; a change in cyoskeleton structure; light; dark; mitogens, including, but not limited to, lipopolysaccharide (LPS), pokeweed mitogen; stress; antigens; sleep pattern (e.g., sleep deprivation, alteration in sleep pattern, and the like); an apoptosis-inducing signal; electrical charge (e.g., a voltage signal); ion concentration of the medium in which a cell is maintained, or an internal ion concentration, exemplary ions including sodium ions, potassium ions, chloride ions, calcium ions, and the like; presence or absence of a nutrient; metal ions; a transcription factor; a tumor suppressor; cell-cell contact; adhesion to a surface; peptide aptamers; RNA aptamers; intrabodies; and the like.

As noted above, excessive heat or excessive cold is relative to the normal range for a cell or multicellular organism. For example, certain archaebacteria live at temperatures in excess of 70° C., e.g., certain archaebacteria have a temperature optimum of about 80° C., about 90° C., about 100° C., or about 110° C. "Excessive" temperature is generally a temperature that is about 5° C., about 10° C., about 15° C. or more, above the temperature optimum for a given cell or organism.

Internal stimuli also include expression of a gene, and production of a gene product. Production of a gene product includes expression of an endogenous gene, and expression of an introduced nucleic acid. In some embodiments, a nucleic acid comprising a nucleotide sequence encoding a protein of interest is introduced into a cell, generating a genetically modified cell, the nucleic acid is expressed, the protein is produced in the genetically modified cell, and the response of the genetically modified cell to the protein is detected. In other embodiments, the nucleic acid encodes a nucleic acid that affects transcription of a gene. Such nucleic acids include antisense nucleic acids, ribozymes, and inhibitory RNA (RNAi) (including double stranded RNAi).

In some embodiments, the protein of interest is an exogenous protein, e.g., a protein that the cell does not normally produce because the cell does not have a nucleic acid encoding such a protein. In other embodiments, the protein of interest is one that a normal cell of the same cell type would normally produce, but that the cell cannot produce because of some defect in the cell. For example, the cell's genome may contain a mutation in the coding region and/or regulatory region of a gene such that a given protein is not produced. Alternatively, the cell's genome may contain a defect in a coding region and/or regulatory region in a gene other than the gene encoding the protein of interest, and introduction of the nucleic acid encoding the protein of interest circumvents the defect. For example, the cell may contain a mutation in a gene encoding a transcription factor necessary for production of the protein of interest, such that the transcription factor is either not produced or is produced in an inactive form, and a nucleic acid is introduced which encodes the protein of interest under control of a promoter not regulated by the absent or defective transcription factor.

In other embodiments, the protein of interest is a dominant negative mutant, e.g., a protein that, when produced, prevents a counterpart normal protein that is produced by the cell from functioning, or reduces the function of the normal protein.

In other embodiments, the protein is an endogenous protein that the cell produces at low levels, and introduction of a nucleic acid encoding the protein results in over-production of the protein. In these embodiments, the coding region of the protein of interest is operably linked to a strong promoter. Strong constitutive promoters that are active in most eukaryotic cell are well known in the art, and include, but are not limited to, human cytomegalovirus immediate early promoter, adenovirus major late promoter, an SV40 virus promoter, a Rous sarcoma virus promoter, and a murine 3-phosphoglycerate kinase promoter.

The nucleotide sequence encoding the protein of interest can be under transcriptional control of an inducible promoter, e.g., a promoter that can be activated by an inducer; a repressible promoter, or a developmentally regulated promoter.

For example, where the nucleotide sequence encoding the protein of interest can be under transcriptional control of an inducible promoter, an external signal includes an inducer of an inducible promoter. Inducible promoters, and their inducers, are well known in the art, and include, but are not limited to, cold-inducible promoters; heat-inducible promoters; metal ion inducible promoters; a tetracycline-inducible promoter; a radiation-inducible promoter; a drug-inducible promoter; a hormone-inducible promoter; and the like. In these embodiments, the nucleic acid is introduced into the cell, and the inducing agent is added to the medium, or the cell is exposed to the inducing condition (e.g., heat, cold, radiation, etc.).

In some embodiments, where a cell is in a liquid medium, an external stimulus is added to the medium, and the response of the cell, as detected by membrane movement, to the external stimulus is monitored. In other embodiments, where the external stimulus is a condition such as heat, cold, radiation, etc., the condition of the cell's environment is adjusted.

The methods are useful for detecting changes in a cell even before the change is detectable visually. For example, a cancerous cell is detected even before the cell undergoes characteristic morphological changes that are visible when viewed under a microscope (e.g., by a clinician). In these embodiments, a cancerous state in a cell is detected in vitro in a biological sample (e.g., a cervical swab, or other tissue biopsy sample) by detecting cell membrane movement, and comparing the movement of the cell membrane with the cell membrane movement characteristic of a normal cell of the same cell type. In this manner, cancerous cells can be detected at a much earlier stage than with means currently available to the clinician.

Atomic Force Microscope

In some embodiments, membrane movement is detected using an atomic force microscope. The method generally involves contacting the cell with an atomic force microscope cantilever probe; and detecting movement of the probe. Membrane movement is used as a read-out for a cell's response to a biochemical event and/or the physiological status of a cell and/or the cell type. The method allows for real-time monitoring of a cell's response to an internal or external stimulus. The methods are useful for detecting a cellular response to an internal or an external signal and are thus useful in applications such as drug screening and diagnostics.

An atomic force microscope generally includes a scanner that has at one end a cantilever. Positioned at the end of the cantilever is a tip, or probe, which rests on the surface of an object, e.g., a membrane of a cell. Vertical movement of the membrane results in movement of the cantilever. Movement of the cantilever is detected by deflection of a laser beam reflected off the cantilever, e.g., off an optical lever attached to the cantilever. Angular deflection of the cantilever causes angular deflection of the laser beam. In the present invention, the AFM is operated in the contact mode. An example is shown in FIG. 1.

The reflected laser beam strikes a position-sensitive photodetector, consisting of a photodiode. Generally, the photodiode is split into four quadrants. The difference in photodiode signals between any two quadrants indicates the position of the laser spot on the detector, and thus the angular deflection of the cantilever. The signals from the photodetector are sent to a data processing means, such as a computer, that processes the data and converts the data to any of a variety of formats. The data can also be stored, and compiled into a database. Vertical movement is detected by the difference in the signal from a first quandrant of a photodiode and the signal from a second quandrant that is positioned above or below the first quandrant. Lateral movement is detected by monitoring the torsional strain on the probe imposed by movement of the membrane in the lateral direction, which is detected by the difference in the signal from a first quandrant of a photodiode and the signal from a second quandrant that is positioned to the left or right of the first quadrant.

The probe is of a radius such that movement of a membrane of a cell can be detected. The end radius of the probe (e.g., the radius of the end of the probe in contact with the membrane) is generally in the range of from about 5 nm to about 50 nm, e.g., from about 5 nm to about 10 nm, from about 10 nm to about 20 nm, from about 20 nm to about 30 nm, from about 30 nm to about 40 nm, or from about 40 nm to about 50 nm.

The probe is contacted with the membrane with a loading force of from about 1.0 pN to about 1.0 µN, e.g., from about 1.0 pN to about 60 pN, from about 0.06 nN to about 0.1 nN, from about 0.1 nN to about 1 nN, from about 1 nN to about 50 nN, from about 50 nN to about 100 nN, or from about 100 nN to about 1.0 µN.

The subject methods detect vertical or lateral movement of a cell membrane of from about 0.1 nm to about 500 nm, e.g., from about 0.1 nm to about 1 nm, from about 1 nm to about 5 nm, e.g., from about 5 nm to about 10 nm, from about 10 nm to about 50 nm, from about 50 nm to about 100 nm, from about 100 nm to about 250 nm, or from about 250 nm to about 500 nm. The subject methods detect movement at a frequency of from about 1 Hz to about 10 kHz, e.g., from about 1 Hz to about 10 Hz, from about 10 Hz to about 50 Hz, from about 50 Hz to about 100 Hz, from about 100 Hz to about 500 Hz, from about 500 Hz to about 1 kHz, or from about 1 kHz to about 10 kHz. The data can be expressed as vertical (or lateral) displacement versus time. In many embodiments, the data are treated with a Fast Fourier Transform (FFT) to generate an amplitude spectrum.

Measurements of membrane movement are made at regular intervals (e.g., every 30 seconds, 60 seconds, two minutes, 5 minutes, 10 minutes, 15 minutes, etc.); or continuously. Alternatively, measurements of membrane movement are made at a single time point, or at random time points.

Where the response of a cell to an external stimulus is analyzed in vitro, the external stimulus is added to the cell medium, as described above. In some embodiments, an external stimulus is added to the medium in which a cell is being analyzed (e.g., cell culture medium, bodily fluid, etc.). In other embodiments, the external stimulus is delivered by the probe itself. In these embodiments, the probe is functionalized or adapted to deliver the signal. In these embodiments, a stimulus is attached to the probe. For example, a drug, a hormone, a nucleic acid, or other signal is attached to the probe, and when the probe contacts the membrane, the stimulus is delivered to the cell. The stimulus is linked to the probe either covalently or non-covalently.

Alternatively, the probe is fitted with an element that delivers the stimulus. For example, a single or multiwall carbon nanotube is attached to the probe, and an external stimulus (e.g, an agent in a liquid formulation) is delivered into the cell (e.g., into the cytoplasm or into the nucleus) by the nanotube. In these embodiments, the stimulus is linked (covalently or non-covalently) to the nanotube. Because of its narrow diameter, the nanotube readily traverses the membrane without adversely affecting the cell, and delivers the signal into the cell. In some embodiments, the stimulus is attached to the nanotube via a linker which is proteolytically cleaved by an intracellular enzyme.

In some embodiments, an element for delivering an electrical signal will be attached to the probe, or is positioned adjacent to the probe, such that an electrical signal is delivered to the membrane.

In some embodiments, a stimulus that is delivered to the cell membrane is a programmable or pre-recorded pattern that is stored in a data storage medium. For example, a stimulus is delivered to the cell at regular intervals (e.g., to mimic a Circadian rhythm). As another example, a stimulus is delivered to a cell to stimulate entry into the cell cycle at a particular time point, which is pre-recorded.

In some embodiments, movement of a membrane of a first cell is converted into a signal, and transmitted to the membrane of a second cell. In some of these embodiments, the first cell is physically separated from the second cell, e.g., the first cell and the second cell are in separate wells of a multi-well plate. In other embodiments, the first cell and the second cell are in the same tissue or colony, but are separated from one another by other cells and/or extracellular matrices. In other embodiments, the first cell and the second cell are in direct contact with one another. Any movement in a membrane of the second cell in response to the signal transmitted from the first cell can be transmitted to a third cell, and so on. An example is depicted schematically in FIG. 3.

In some embodiments, a single probe is in contact with a cell. In other embodiments, two, three, four, or more, individual probes are in contact with a membrane of a cell. For example, individual probes are in contact with different areas of a cell membrane. This embodiment is illustrated in FIG. 2B. An example of a situation in which use of multiple probes is useful is in analyzing cells in which different areas of the cell respond differentially to a given stimulus. Non-limiting examples of such cells are polarized cells (e.g., columnar epithelial cells lining the gastrointestinal tract); and cells that have processes that extend from the cell body (e.g., neuron, axons, dendritic cells, etc.).

The data transmitted by the position-sensitive detector to the data processor can be formatted in several different ways. Generally, the data are treated with a FFT to generate an amplitude spectrum. The data can also be converted into audio or color format. Conversion into audio format is accomplished using standard audio conversion software, and allows a qualitative measure of the physiological status of a cell. In addition, rather than representing the amplitudes as peaks, color intensities can be used to represent peak intensities, and a plot of each short FFT versus time can be made, resulting in a sonogram. For example, the data can be converted into a usable format in real time using Fourier Transformation Filtering, Audio Files, Color Spectra, and the like.

Movement of a membrane in response to a given stimulus will generally be characteristic for the type of response to the stimulus. The subject method allows determination of the characteristic FFT amplitude spectrum for different cell types, and for different physiological status of a given cell type. For example, movement of a cell membrane during mitosis will produce a characteristic FFT amplitude spectrum. In addition, the FFT amplitude spectrum differs for different cell types and thus allows detection of a given cell type in a sample containing multiple cell types. Differences in the FFT amplitude spectrum can be used to detect a cancerous cell of a given cell type.

AFM Arrays

The invention further provides a method of determining a cell characteristic in a plurality of cells. The method generally involves contacting each cell of a plurality of cells with a probe of an atomic force microscope (AFM) in an array of AFM; and detecting movement of the probes. In some embodiments, the array is a two-dimensional array. In other embodiments, the array is a three-dimensional array. These embodiments are illustrated in FIGS. 4A-4B. In some embodiments, the cells are in a colony or in a tissue. AFM cantilever arrays have been described in the literature. See, e.g., Minne et al. (1998) *Applied Physics Letters* 78:2340-2342; Lang et al. (1998) *Appl. Phys. Lett.* 72:383; Baller et al. (2000) *Ultramicroscopy* 82:1-9; Britton et al. (2000) *Ultramicroscopy* 82:17-21; McKendry et al. (2002) *Proc. Natl. Acad. Sci. USA* 99:9783-9788.

In some embodiments, the cells are isolated, and each individual cell is brought into contact with a separate probe. A microfluidics device or other device can be used to isolate the cells. For example, a fluorescence activated cell sorter is used to isolated individual cells, which are then contacted with individual probes. Cells can be isolated in individual microcavities. See, e.g., U.S. Pat. No. 6,377,721.

In some embodiments in which an array of probes are used, the movement of a membrane in a first cell is converted into a signal and transmitted into at least a second cell, as described above.

In some embodiments, each cantilever probe is fitted with a nanotube, and each nanotube is linked with a different signal. For example, a first nanotube associated with a first probe has linked thereto (e.g., is coated with) a first agent, which is delivered to a first cell, and a second nanotube associated with a second probe has linked thereto a second agent, which is delivered to a second cell, and so on. Such an array is useful for drug screening. Such an array is also useful for gathering data regarding the response of a given cell type to various signals.

In other embodiments, the probes are themselves functionalized to deliver agents to cell membranes of individual cells, or spatially separated cells. For example, a first probe in an array is functionalized with a first agent, which is delivered to the membrane of a first cell, and a second probe in an array is functionalized with a second agent, which is delivered to the membrane of a second cell, and so on.

Micromirror-Based Detection

In some embodiments, the invention provides a method for determining a cell characteristic, involving monitoring the movement of a mirror attached to the cell surface. Use of a mirror attached to a cell surface is particularly useful for analyzing soft cells, such as mammalian cells.

For example, where the cell characteristic is determined by monitoring cell membrane movement, cell membrane movement is analyzed by detecting movement of a mirror (also referred to herein as a "reflector," a "micromirror," or a "quantum nanomirror") attached to the surface of the cell. As used herein, the term "reflector" is used to denote a body which reflects a portion of the electromagnetic radiation incident on the body. An incident beam of light is reflected by the mirror. Movement of the mirror is detected by a sensor which detects the reflected beam of light.

As another example, the movement of an entire cell can be monitored in vitro. Movement of a cell includes lateral movement and vertical movement. The movement of a cell is in some embodiments monitored in an in vitro culture, wherein the cells are detached from one another. In other embodiments, movement of a cell in an in vitro culture system involves monitoring movement of a cell across a monolayer of adherent cells. In other embodiments, movement of a cell in an in vitro culture system involves monitoring movement of a cell in a tissue. In still other embodiments, movement of a cell in an in vitro culture system involves monitoring adhesion of a first cell to a second cell that comprises on its cell surface a receptor for a ligand present on the surface of the first cell, or that comprises a co-receptor for a receptor present on the surface of the first cell. As one non-limiting example, metastasis of a tumor cell can be monitored in in vitro cell culture assay. As another non-limiting example, leukocyte homing and extravasation can be monitored in an in vitro assay.

In these embodiments, light, e.g., a laser beam, is directed onto a mirror attached to the surface of a cell, and the position of a reflected laser beam is detected by a sensor. For example, a first position of a laser beam reflected by a mirror attached to a cell surface is detected at a first time; and a second position of a laser beam reflected by the mirror is detected at a second time. Where the second position differs substantially from the first position indicates movement of the cell membrane (including movement of the entire cell).

Measurements of membrane movement are made at regular intervals (e.g., every 5 seconds, 10 seconds, 20 seconds 30 seconds, 60 seconds, two minutes, 5 minutes, 10 minutes, 15 minutes, etc.); or continuously. Alternatively, measurements of membrane movement are made at a single time point, or at random time points.

Where the response of a cell to an external stimulus is analyzed in vitro, the external stimulus is added to the cell medium, as described above. In some embodiments, an external stimulus is added to the medium in which a cell is being analyzed (e.g., cell culture medium, bodily fluid, etc.).

Mirrors

The present invention provides mirrors for use in a subject method for detecting cell movement. Typically, a subject mirror comprises a reflector surface and a cell attachment surface. In some embodiments, the reflector surface has an optical grating texture (a diffraction grating) that diffracts light. The attachment surface is derivatized with one or more different cell attachment moieties which provide for attachment to a cell surface.

Mirrors suitable for attachment to the cell surface are any of a variety of shapes, e.g., circular, oval, square, ellipsoid, rectangular, an irregular shape, etc. In many embodiments, a subject micromirror is generally disc shaped. Typically, the surface area of the mirror is less than about 50%, less than about 40%, less than about 30%, less than about 20%, less than about 10%, less than about 5%, less than about 2%, or less than about 1% of the surface area of the cell. For example, in general, the surface area of a subject micromirror is in a range of from about 75 $nm^2$ to about 25 $\mu m^2$, e.g., from about 75 $nm^2$ to about 100 $nm^2$, from about 100 $nm^2$ to about 150 $nm^2$, from about 150 $nm^2$ to about 200 $nm^2$, from about 200 $nm^2$ to about 500 $nm^2$, from about 500 $nm^2$ to about 750 $nm^2$, from about 750 $nm^2$ to about 1 $\mu m^2$, from about 1 $\mu m^2$ to about 2 $\mu m^2$, from about 2 $\mu m^2$ to about 5 $\mu m^2$, from about 5 $\mu m^2$ to about 10 $\mu m^2$, from about 10 $\mu m^2$ to about 15 $\mu m^2$, from about 15 $\mu m^2$ to about 20 $\mu m^2$, or from about 20 $\mu m^2$ to about 25 $\mu m^2$.

The diameter of a mammalian cell ranges from about 3 μm to about 11 μm. Thus, for example, where the mirror is circular in shape, and the cell is a mammalian cell, the mirror generally has a diameter in the range of from about 10 nm to 5 μm, e.g., from about 10 nm to about 50 nm, from about 50 nm to about 100 nm, from about 100 nm to about 250 nm, from about 250 nm to about 500 nm, from about 500 nm to about 750 nm, from about 750 nm to about 1 μm, from about 1 μm to about 2 μm, or from about 2 μm to about 5 μm.

The reflector surface of a subject mirror comprises any of a variety of materials. Suitable materials for the reflector surface include, but are not limited to, silicon dioxide, polydimethylsiloxane (PDMS), silicon nitride (SiNx), and the like. In some embodiments, a subject mirror comprises biodegradable materials.

The reflector surface of a subject mirror will in some embodiments comprise an optical grating texture (a "diffraction grating") that diffracts light. The diffraction grating is in any of a variety of patterns, e.g., a linear array, a radial array, a spiral array, and the like. In addition, the pitch of the grating can vary. See, e.g., "Diffraction Grating" 5$^{th}$ edition, C. Palmer (2004) Spectra-Physics, Inc. For example, the pitch can vary from about 0.1 μm to about 10 nm, e.g., from about 0.1 μm to about 0.5 μm, from about 0.5 μm to about 1 μm, from about 1 μm to about 10 μm, from about 10 μm to about 50 μm, from about 50 μm to about 100 μm, from about 100 μm to about 500 μm, from about 500 μm to about 1 nm, from about 1 nm to about 5 nm, or from about 5 nm to about 10 nm.

In some embodiments, the grating pattern provides information as to the identity of the attachment molecule(s) on the attachment surface of the mirror. Thus, in these embodiments, the diffraction grating pattern provides a code as to the identity of the attachment molecule or combination of attachment molecules on the attachment surface.

Attachment Moieties

The attachment surface of the mirror is attached to the surface of a cell by any of a number of interactions, including electrostatic interactions, steric stabilization, van der Waals forces, covalent linkage, and the like. In many embodiments, an attachment moiety is attached to (immobilized on) the attachment surface of the mirror, where the attachment moiety provides for attachment of the mirror to the cell surface. In some embodiments, an attachment moiety is synthesized directly on the attachment surface of the mirror. See, e.g., U.S. Pat. No. 6,630,308. In other embodiments, a preformed attachment moiety is attached to (immobilized on) the attachment surface by chemical coupling, adsorption or other means. A large number of immobilization techniques have been used and are well known in the fields of solid phase immunoassays, nucleic acid hybridization assays and immobilized enzymes. See, for example, Hermanson, Greg, T. Bioconjugate Techniques. Academic Press, New York. 1995, 785 pp; Hermanson, G. T., Mallia, A. K. & Smith, P. K. Immobilized Affinity Ligand Techniques. Academic Press, New York, (1992) (Chapter 5); and Avidin-Biotin Chemistry: A Handbook. D. Savage, G. Mattson, S. Desai, G. Nielander, S. Morgansen & E. Conklin, Pierce Chemical Company, Rockford Ill., 1992, 467 pp; Protein Immobilization, Fundamentals & Applications, R. F. Taylor, ed. (1991) (chapter 8).

Attachment moieties include a wide variety of biomolecules, including, but not limited to, nucleic acids, including DNA, RNA, oligonucleotides; proteins (including phosphoproteins, lipoproteins, glycoproteins, and the like), peptides; lipids, fatty acids; polysaccharides, oligosaccharides; organic polymers; any of a wide variety of organic molecules which include one or more moieties for binding to a cell surface biomolecule; antibodies; ligands (e.g., agonists for a cell surface receptor, an antagonist for a cell surface receptor); microorganisms; receptors; antibiotics; test compounds (e.g., compounds produced by combinatorial chemistry); bacteria; viruses; and plant and animal cells and organelles or fractions thereof.

An attachment moiety is bound to (immobilized onto) the attachment surface of the mirror. The mirror is bound to the cell surface. The term "bind" includes any physical attachment or close association, which may be permanent or temporary. Generally, an interaction of hydrogen bonding, hydrophobic forces, van der Waals forces, covalent bonding, etc. facilitates physical attachment between the attachment moiety and the attachment surface. Generally, an interaction of hydrogen bonding, hydrophobic forces, van der Waals forces, etc. facilitates physical association between an attachment moiety and a cell surface molecule.

The attachment surface of the mirror comprises any material onto which an attachment moiety can be immobilized, or that can be derivatized or otherwise processed such that an attachment moiety can be immobilized onto the attachment surface. Suitable attachment surface materials include, but are not limited to, polymers, plastics, resins, polysaccharides, silica or silica-based materials, carbon, metals, inorganic glasses, membranes, particles, gels, functionalized glass, germanium, silicon, GaAs, GaP, SiO2, SiN4 modified silicon, polytetrafluoroethylene, polyvinylidenedifluoride, polystyrene, polycarbonate, flat glass, or single-crystal silicon, polytetrafluorethylene, polystyrene, gallium arsenide, or combinations thereof. Suitable polymers include, but are not limited to, (poly)tetrafluoroethylene, (poly)vinylidenedifluoride, polystyrene, polycarbonate, and polymerized Langmuir-Blodgett film.

The attachment surface of a subject mirror is in many embodiments functionalized to include one or more attachment sites for attaching to the cell surface, or for attaching an attachment moiety. Suitable functional groups include, but are not limited to, sulfhydryl groups, and the like.

The attachment surface may be coated with a material that facilitates attachment of an attachment moiety. Some solid phase surfaces may be used directly to immobilize an attachment moiety, others must be modified to allow such attachments. For example, antibodies and many other proteins will adhere to clean polystyrene surfaces. Polystyrene, either in the form of microtiter plates or beads, have been modified to bind nucleic acids, proteins, and polysaccharides using techniques that are well known. Teflon™ surfaces will bind proteins or other macromolecules that have been suitably fluorinated (see, e.g., U.S. Pat. No. 5,270,193). and will also bind fluorinated surfactants, which may render the surface hydrophilic, or positively or negatively charged. Glass, including controlled pore glass, may be modified to allow covalent attachment of antibodies, antigens or nucleic acids. Plastic or glass surfaces may be modified non-specifically using corona plasma discharge or electron beam radiation and may then be coated with a variety of coatings or adhesives to which an attachment moiety may be attached. More specific covalent attachment of proteins, nucleic acids or carbohydrates may be achieved by a variety of modifications which attach reactive groups to polystyrene or acrylic surfaces, which groups, with or without extending linkers, will then couple under mild conditions to the biopolymers.

In addition to methods by which an attachment moiety is immobilized on a solid surface, general methods exist for immobilizing members of a class of attachment moiety. For example, protein A or protein G may be immobilized and used to subsequently bind specific antibodies which in turn will bind specific ligands. A more general approach is built around the strong and specific reaction between other ligands and receptors such as avidin and biotin. Avidin may be immobilized onto the attachment surface, and used to bind antibodies or other biomolecules to which biotin has been covalently linked. This allows the production of surfaces to which a very wide variety of reactants can be readily and quickly attached (see Savage et al., Avidin-Biotin Chemistry: A Handbook. Pierce Chemical Company, 1992).

In some embodiments, the attachment moiety is a first member of a specific binding pair, where the second member of the specific binding pair is displayed on the cell surface. Non-limiting examples of specific binding pairs include selectin/selectin ligand; viral antigen/cell surface receptor; antibody/antigen; receptor/ligand; extracellular matrix/integrin; and the like. Thus, e.g., the first member of a specific binding pair is one or more of the following: an antibody (or an epitope-binding fragment thereof) specific for an epitope displayed on a cell surface; a ligand for a cell surface receptor; a portion of an extracellular matrix molecule that is bound by a cell surface receptor; a carbohydrate moiety that is recognized by a cell surface selectin; and the like.

Viral antigens that are suitable for attachment to the attachment surface of a subject mirror include, but are not limited to, any viral attachment protein, e.g., a viral env protein, a viral spike protein, a viral fusion protein, a viral capsid protein, and the like, including, e.g, human immunodeficiency virus (HIV) gp160 and gp120; human rhinovirus 14; tick-borne encephalitis virus E protein; influenza virus hemagglutinin; respiratory syncytial virus fusion protein F; adenovirus fiber protein; reovirus attachment protein σ1; SARS coronavirus S(S1) protein; herpes simplex virus-1 glycoprotein D; poliovirus capsid shell (VP1, VP2, VP3); and the like. Viral entry proteins are well described in the literature. See, e.g., Dimitrov (2004) Nature 2:109-122.

Suitable agonists and antagonists that bind a cell surface receptor include, but are not limited to, hormones; neurotransmitters; cytokines; chemokines; pharmaceutical agents; derivatives of any of the foregoing that have altered properties compared to a naturally-occurring agonist or antagonist; and the like.

In some embodiments, the attachment moiety is specific to a cell type. In other embodiments, the attachment moiety provides attachment to a wide variety of cells. Non-limiting examples of attachment moieties that are specific to particular cell types include L-selectin ligands, where L-selectin ligands include sulfated forms of GlyCAM-1, CD34 and MAdCAM-1, and where L-selectin is displayed on the surface of leukocytes; E-selectin ligands, where E-selectin ligands tetrasaccharides such as Sialyl-Lewis$^x$ and Sialyl-Lewis$^a$, and cutaneous lymphocyte-associated antigen, and where E-selectin is found on the surface of endothelial cells; and antibodies to cell-specific cell surface molecules. Suitable attachment moieties include proteins bound by cell surface integrins, where suitable attachment moieties include laminin, collagen, fibronectin, tenascin, α4β1, α4β7, VCAM-1, MAdCAM-1, ICAM-1, ICAM-2, ICAM-3, fibrinogen, vitronectin, and the like. Suitable attachment moieties include integrins such as α4β1, α4β7, and the like. Suitable attachment moieties include antibodies specific for macromolecules displayed on a cell surface, where exemplary cell surface macromolecules include tumor-associated antigens; cell surface receptors; viral proteins (e.g., viral proteins displayed on the surface of a virus-infected cell); and the like.

In some embodiments, the attachment moiety is an antibody specific for a tumor-associated antigen. Tumor-associated antigens (TAA) include, but are not limited to, MAGE-2, MAGE-3, MUC-1, MUC-2, HER-2, high molecular weight melanoma-associated antigen MAA, GD2, carcinoembryonic antigen (CEA), TAG-72, ovarian-associated antigens OV-TL3 and MOV18, TUAN, alpha-feto protein (AFP), OFP, CA-125, CA-50, CA-19-9, renal tumor-associated antigen G250, EGP-40 (also known as EpCAM), S100 (malignant melanoma-associated antigen), p53, and p21ras.

Typically, the attachment surface comprises a plurality of attachment moieties, e.g., the attachment surface of a single micromirror comprises from about 10 to about $10^{10}$ or more attachment moieties, e.g., from about 10 to about 100, from about $10^2$ to about $10^3$, from about $10^3$ to about $10^4$, from about $10^4$ to about $10^5$, from about $10^5$ to about $10^6$, from about $10^6$ to about $10^7$, from about $10^7$ to about $10^8$, from about $10^8$ to about $10^9$, or from about $10^9$ to about $10^{10}$, or more, attachment moieties.

In some embodiments, the attachment surface comprises a plurality of attachment moieties, wherein the plurality of attachment molecules is homogeneous, e.g., all the attachment molecules on the surface of a single mirror are identical. In other embodiments, the attachment surface comprises a plurality of attachment moieties, wherein the plurality of attachment moieties is heterogeneous, e.g., the plurality of attachment moieties comprises at least two, at least 3, at least 4, at least 5, at least 6, at least 7, at least 8, at least 9, or at least 10, or more, different attachment moieties.

In some embodiments, the attachment moiety itself provides an external stimulus to the cell, and the response of the cell to the attachment moiety is monitored by detecting cell membrane movement. In other embodiments, the attachment surface comprises an attachment moiety; and an agent that provides an external stimulus to the cell.

In some embodiments, a single mirror is attached to a single cell. In other embodiments, a plurality (two or more) of mirrors are attached to a single cell. An example of a situation in which use of multiple mirrors is useful is in analyzing cells in which different areas of the cell respond differentially to a given stimulus. Non-limiting examples of such cells are polarized cells (e.g., columnar epithelial cells lining the gastrointestinal tract); and cells that have processes that extend from the cell body (e.g., neurons, axons, dendritic cells, etc.).

Arrays

In some embodiments, the invention provides arrays of micromirrors. In some embodiments, each member micromirror in a subject micromirror array comprises an attachment surface with a different attachment moiety from other array members.

Mirror Fabrication

Mirrors are fabricated using any of a variety of methods known in the art. Suitable techniques include silicon micromachining; SiNx micromachining; contact printing; dip pen lithography; lift off techniques; and the like. In many embodiments, the micromirror comprises a crystal material such as silicon.

Sensors

Suitable sensors include any device that is capable of detecting a reflected beam of light. Suitable sensors include, but are not limited to, charge coupled devices (CCD). The CCD camera is connected to an image analysis computer system for data storage and analysis. The scanning process establishes a series of spatial mirror coordinates and mirror types of all the mirrors on the sample.

In some embodiments, two-dimensional arrays of micromirrors are used. Arrays of source beams of vertical cavity surface emitting laser (VCSEL) is directed at a two-dimensional array of mirrors. VCSELs can provide a source beam having substantial light intensity, without requiring additional lensing or amplification, in a focused area with low-beam divergence. The deflected beams are identified and detected using a second array of micromirrors which defect the beams to an array of detectors (e.g., a two-dimensional array of photodetectors).

Databases

Also provided are databases of profiles of cell characteristics. Such databases will typically comprise profiles of cell membrane movement of various cell types; cell membrane movement of cells of various biological states; and cell membrane movement of cells in response to various biochemical events. A cell membrane characteristic profile will contain, in addition to the cell membrane movement profile, one or more of the following cell parameters: cell type; biochemical event that stimulated the cell membrane movement; cellular environment, e.g., culture conditions, such as media composition and conditions, temperature, pH, osmolarity, etc.; physiological status of the cell. Thus, a cell characteristic profile includes the cell membrane movement profile and at least one additional cell parameter.

The cell characteristic profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as compact disc read only memory (CD-ROM); electrical storage media such as random access memory (RAM) and ROM; and hybrids of these categories such as magnetic/optical storage media. One of skill in the art can readily appreciate how any of the presently known computer readable media can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage and processing means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. One format for an output means ranks cell characteristic profiles possessing varying degrees of similarity to a reference profile. Such presentation provides a skilled artisan with a ranking of similarities and identifies the degree of similarity contained in the test profile.

A subject database is useful for comparing a test profile to a reference profile that is stored in the database. Thus, the invention provides methods of identifying or determining a characteristic of a cell, involving comparing a test profile of a cell with a database of profiles. For example, a cell profile that is generated in a clinical setting by analyzing a lung biopsy sample (the "test profile") is compared to one or more reference profiles stored in the database, where the reference profiles contain characteristics of normal (non-cancerous) lung cells, various types of cancerous lung cells, etc. Based on the comparison to the database, a determination of a characteristic of the test profile is made.

The invention further provides methods of obtaining a cell characteristic profile, and methods of generating a database, or collection, of cell characteristic profiles. The methods generally involve detecting membrane movement of a cell, storing the membrane movement data on a computer readable medium (CRM), and linking the data with at least one additional data about the cell (e.g., cell type, biological state, biological event which resulted in the membrane movement, cell medium conditions, and the like), thereby generating a profile. The cell profile is recorded on a CRM. A database includes a plurality of such profiles. In some embodiments, the cell profile is represented in a visual format. In other embodiments, the cell profile is represented in a sound format. In other embodiments, the cell profile is represented in a color format.

Where the data are generated using a micromirror-based analytical system as described above, the data are generated and stored in the form of the degree of deflection of a reflected beam of light compared to a control.

Where the data are generated using AFM, data are typically generated and stored in the form of FFT amplitude spectra (or, alternatively, in other formats, such as color sonograms, as discussed above). Data include the FFT amplitude spectrum that is characteristic for the movement of a cell membrane of a given cell type, the FFT amplitude spectrum that is characteristic for the movement of a cell membrane in a given physiological condition, the FFT amplitude spectrum that is characteristic for the movement of a cell membrane of a given cell type in a given physiological status, and the FFT amplitude spectrum that is characteristic for the response of a given cell type to a biochemical event.

The data are obtained by measuring the cell membrane movement of a wide variety of cell types. The membrane movement of each cell type is recorded under various conditions. As one non-limiting example, cell membrane movement of a myocyte is measured in media of various pH, in media containing various agents (e.g., adrenaline, a calcium ionophore), in media containing various ion concentrations, in media containing agents that induce a conditions that mimics a disease state, under normal physiological conditions, and the like. The FFT amplitude spectrum is recorded for each condition, and information regarding the condition is entered into the database, such that the two pieces of information are linked. The information in the database is searchable using terms for the cell type, and cell conditions. In another non-limiting example, cell membrane movement of a $CD4^+$ T lymphocyte is recorded under normal physiological conditions (e.g., in serum), the cell membrane movement of a $CD4^+$ T lymphocyte that is infected with human immunodeficiency virus is recorded, and the cell membrane movement of various T cell leukemias are recorded and stored in the database.

Systems

The invention further provides a system for determining a characteristic of a cell. A subject system generally includes at least a membrane movement responsive element; and a detection element for detecting a signal generated by the responsive element; and a data storage and processing means, for storing the signal, for converting the signal to various formats, for comparing the signal to other stored signals, etc. Data storage and processing means are computer-based systems, as described above.

In some embodiments, where the detection system involves use of a micromirror attached to a cell surface, a subject system includes a light source (e.g., a laser light source), a sensor, such as a CCD, and a data storage and processing means.

In some embodiments, the system includes at least one atomic force microscope and a data storage and processing means. In some of these embodiments, the AFM includes, in addition to a cantilever probe, a nanotube or other element for delivering a stimulus to a cell. In some embodiments, the system includes an AFM array, e.g., for processing a plurality of cell samples.

In other embodiments, the system further includes an endoscope, where the membrane movement responsive element is mounted on the distal end of the endoscope. The distal end of the endoscope can further include other sensors, including, but not limited to, piezoelectric films, AFM cantilevers, pressure sensors, capacitance diaphragm in MEMS, etc. An array of sensors enables computer software to remove background noise and isolate cell motion to apex location. Further, mechanical actuators are used for cell therapy, and are combined with techniques for tumor removal, such as lasers, etc.

Utility

The methods of the invention find use in a variety of applications, including drug screening, detection assays, and diagnostic assays.

Screening Assays

The invention provides screening assays for identifying agents that affect a cell process and/or physiological status. The methods generally involve contacting a cell with a test agent, and determining the effect, if any, on membrane movement. The invention further provides assays for detecting the presence of an analyte in a test sample. The methods generally involve contacting a cell with a test sample; and detecting any change in cell membrane movement in response to the test sample.

Screening for Activity of a Test Agent

Thus, the invention provides screening assays for identifying agents that affect a cell process and/or physiological status. The methods generally involve contacting a cell with a test agent, and determining the effect, if any, on membrane movement. Such a screening assay is useful to identify agents that affect a biological process and/or a physiological status of a cell. For example, an agent that inhibits mitosis, and which therefore may be of use in treating cancer, is identified by monitoring cell membrane movement that is characteristic of a cell undergoing mitosis.

The terms "candidate agent," "agent," "substance," and "compound" are used interchangeably herein. Test agents encompass numerous chemical classes, typically synthetic, semi-synthetic, or naturally-occurring inorganic or organic molecules. Test agents may be small organic compounds having a molecular weight of more than 50 and less than about 2,500 daltons. Test agents may comprise functional groups necessary for structural interaction with proteins, particularly hydrogen bonding, and may include at least an amine, carbonyl, hydroxyl or carboxyl group, and may contain at least two of the functional chemical groups. The test agents may comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Test agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible. Additionally, natural or synthetically produced libraries and compounds are readily modified through conventional chemical, physical and biochemical means, and may be used to produce combinatorial libraries. Libraries of test agents also include cDNA libraries, e.g., expression libraries from a given cell type, from a cell in response to an agent, from a cell of a given physiological status (e.g., a cancerous cell), and the like.

Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Assays of the invention include controls, where suitable controls include a sample (e.g., a cell sample) in the absence of the test agent. Generally a plurality of assay mixtures is run in parallel with different agent concentrations to obtain a differential response to the various concentrations. Typically, one of these concentrations serves as a negative control, i.e. at zero concentration or below the level of detection.

Agents that have an effect in an assay method of the invention may be further tested for cytotoxicity, bioavailability, and the like, using well known assays. Agents that have an effect in an assay method of the invention may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity and/or ability to cross the blood-brain barrier.

The components of the assay mixture are added in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

In many embodiments, an array of isolated cells or colonies of cells is used, wherein each isolated cell or colony of cells is contacted with a test agent, and the effect on the cells is determined by contacting the cells or cell colony with an array of AFM probes. In some embodiments, the cell array is addressable, such that the identity of each isolated cell/cell colony is known and can be matched to the cell's reaction to the test agent. For example, cells are deposited on discrete regions (e.g., microwells) of a solid substrate, and each microwell contains a unique identifier that corresponds to the identity of the cells in the microwell. Alternatively, the cells themselves are encoded with at least one optically interrogatable material, such as a bioluminescent compound, a chemiluminescent compound, a chromophore, a fluorophore, etc. See, e.g., U.S. Pat. No. 6,377,721.

Detecting the Presence of an Analyte

The invention further provides assays for detecting the presence of an analyte in a test sample. The methods generally involve contacting a cell with a test sample; and detecting any change in cell membrane movement in response to the test sample. Such a screening assay is useful to detect the presence in a sample of an analyte suspected to exist in the sample, e.g., a subject screening assay can be used to detect the presence in a sample of a toxin or a toxic bacterium, e.g., an environmental agent (e.g., a pesticide, an herbicide, an environmental toxin, and the like), an agent of chemical or biological warfare (e.g., nerve gas, anthrax, etc.).

Assays of the invention include controls, where suitable controls include a sample (e.g., a cell sample) in the absence of the test sample. Generally a plurality of assay mixtures is run in parallel with different known concentrations of the analyte being detected to obtain a differential response to the various concentrations. Typically, one of these concentrations serves as a negative control, i.e. at zero concentration or below the level of detection.

The assay methods provide for qualitative (e.g., presence or absence), semi-quantitative, and quantitative detection of analyte. Where the methods are quantitative, the response of a cell membrane to a test sample is compared to a standard curve obtained using known concentrations of the analyte, and the presence and concentration of the analyte are determined.

Diagnostic Assays

The methods of the invention are useful for identifying a characteristic of a test cell. Methods for identifying a characteristic of a test cell generally involve determining a cell characteristic profile of the test cell to generate a test profile, and comparing the test profile with a reference profile in a subject database. Such comparison provides the best match, e.g., identifies a reference profile that is substantially identical to the test profile. The reference profile provides a characteristic of the test cell.

As an example, the methods of the invention are useful for detecting the presence in a tissue or a biological sample of a cell that is abnormal. Because the cell membrane movement is characteristic for a given cell type, and also for cancerous cells of a given cell type, determination of the cell membrane movement of a given cell provides information as to whether the cell is undergoing mitosis at a rate characteristic for the cell type, or is dividing in an uncontrolled manner, e.g., is cancerous. The methods are also useful for providing the cell type of the cancerous cell. The methods are further useful for staging the cancer.

The cell characteristic profiles are compiled in a database, as described above, and the information in the database is used to compare the profile of a test cell to a reference profile in the database. The comparison can be made by trained personnel (e.g., a clinician, a technician, etc.), or can be made by a computer or other machine.

The subject diagnostic assays are useful for identifying any type of abnormal cell, e.g., For example, diagnostic assays of the invention are useful for identifying cancerous cells in a biological sample, e.g., a biopsy, as well as in an individual in vivo.

Treatment Methods

The invention further provides a method of treating a disease or disorder; The methods generally involve identifying a characteristic of a cell, which characteristic indicates that the cell is abnormal; and recommending a treatment regimen appropriate to the abnormality.

For example, where a cell in a tissue biopsy is determined to be a cancerous cell, a treatment regimen appropriate to the particular type of cancer is recommended. In some embodiments, as discussed above, the methods provide for staging of the cancer. A course of chemotherapy or radiation therapy appropriate to the stage of the cancer is then recommended.

Neural Networks

The data obtained from analysis of various cell types under various physiological conditions and in various physiological states is compiled in a database in order to train neural networks for independent detection of cell types and physiological status of cells. The cell characteristic profiles are obtained as described above, and the neural network is trained to recognize cells of various cell types, cells in various physiological states, and cells responding to various stimuli. The neural network is useful for identifying cancerous cells, pre-cancerous cells, and cells in other pathological conditions.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Use of AFM to Determine a Cell Characteristic

Materials and Methods
Yeast Strains and Growth Conditions

The *Saccharomyces cerevisiae* strains used are BY4741 (MATa his3 leu2 met15 ura3), W303.1B (MAT a ade2-1, his3-11, 15, leu2-3, 112, trp1-1, ura3-1) and CC304.1 (W303.1B-atp2Δ2:LEU2), which is a respiratory-deficient mutant strain. Cells were grown in YPD medium (2% peptone, 1% yeast extract, and 2% glucose) incubated at 30° C. with shaking at 220 rpm, and grown for 16 to 20 hours (Kaiser et al. (1994) Cold Spring Harbor Laboratory Press, Cold Spring Harbor, N.Y.).

Atomic Force Microscopy

All measurements were made with a Nanoscope IV (Bioscope, Veeco Digital Instruments, Santa Barbara) using a fluid cell. In most experiments $SiN_4$ triangular cantilevers (0.06 N/m spring constant) were used. Cantilevers with 0.12 N/m spring constants were also used to discriminate against experimental artifacts that might be associated with the cantilever spring constant. Sensitive motion detection with the AFM requires special attention to vibration-isolation and electrical and thermal noise inherent in experimental systems. In order to achieve high sensitivity the microscope was housed on a vibration-isolation air table inside an acoustic isolation chamber that also shields out electrical noise and thermal drift. The entire system was then placed inside a soundproof room and all electronics (computers, controllers, pumps) were kept outside which allows the operator to conduct experiments from another room. With all these precautions in place the vertical noise level was determined to be 0.06 nm (RMS).

Cellular Motion Detection

Cells were immobilized on freshly cleaved mica (Ted Pella, Redding, Calif.) coated with 1 mg/ml Concanavalin A (Sigma Aldrich) as described previously (Gad et al. (1997) *Cell Biol. Int.* 21:697-706). The cells were imaged in contact mode and a cell was chosen to study. The tip was positioned on top of the chosen cell and then the scan size was set to 0 nm in order to keep the position of the tip constant. A force curve was measured to minimize contact force and verify that the tip was still in contact with the cell wall. The vertical deflection of the cantilever was recorded in deflection mode with a sampling rate of 40 kHz. The data that was recorded in real-time was Fast Fourier Transformed (FFT) in order to study the frequency characteristics of the motion. Cells were killed by exposure to ethanol for 60 minutes and membrane motion was then measured and analyzed in the same manner. As a control, cells were also left to die naturally in a test tube and showed similar frequency characteristics as the cells killed by ethanol. Control experiments can be performed to rule out experimental artefacts that may be causing the observed cellular movement. By bringing the tip into contact with glass or mica or rubber or left free in the air and the measurement can be made and analyzed in the same manner as the cellular movement data.

Force Experiments

By adjusting the force curve the contact force can be varied and was usually set at or below 12 nN. The force exerted by the AFM tip on each cell type was increased or removed in 5 nN increments by adjusting the set point voltage. The AFM allows for direct mechanical perturbation and simultaneous recording of the cellular response. The applied force could be cycled by increasing and decreasing the amount of force in 5 nN steps over a range of forces from 10 nN to 100 nN. This type of force cycling was repeated three times for each cell studied.

Sonocytology

The position data of the cell motion is a 16-bit data set, which was converted into real time .wav format with simple audio conversion software and no other processing was carried out. This resulting sound file was analyzed in an audio processing program with spectrum analysis in order to create a sonogram. Sonograms were generated from the FFT in microsecond segments of the sound file as a function of time where a color look up table is used to represent peak intensities.

Results

Figure 4:
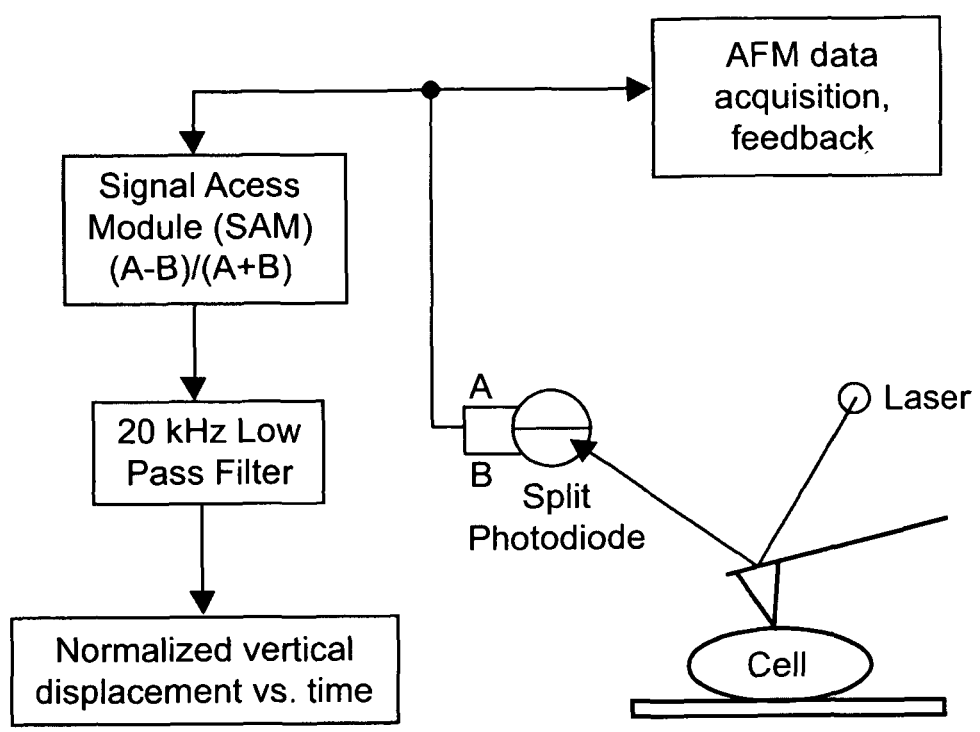
FIG. 4 depicts a schematic of the experimental setup. The AFM is first used to image a single cell and then the cantilever is positioned on top of the cell and its vertical deflection is recorded in real time.

Three strains of the yeast *Saccharomyces cerevisiae* were investigated. Two commonly used wild-type laboratory strains BY4741 (Brachmann et al., (1998) *Yeast* 14:115-132) and W303.1B (Tzagoloff et al., (1986) *J. Biol. Chem.* 261: 17163-17169), and a third, CC304.1 (Do et al., (1996) *Proc. Natl. Acad. Sci. USA.* 93:7534-7539; Yang et al., (1998) *J. Biol. Chem.* 273:31337-31344), a mutant derived from W303.1B which is unable to respire ("respiratory-incompetent") and obtains energy solely from glycolysis (fermentation). Each cell imaged here was at the end of the log phase (Johnston et al., (1992) Gene Expression. Cold Spring Harbor Laboratory Press, Cold Spring Harbor, N.Y.) when the cells are not dividing rapidly and are moving into stationary phase. A schematic depiction of the analysis is shown in FIG. 4. A cell was chosen to study from the AFM image and the cantilever was positioned on top of the cell in order to measure the vertical movement of the cell wall (see methods section).

Figure 5A:
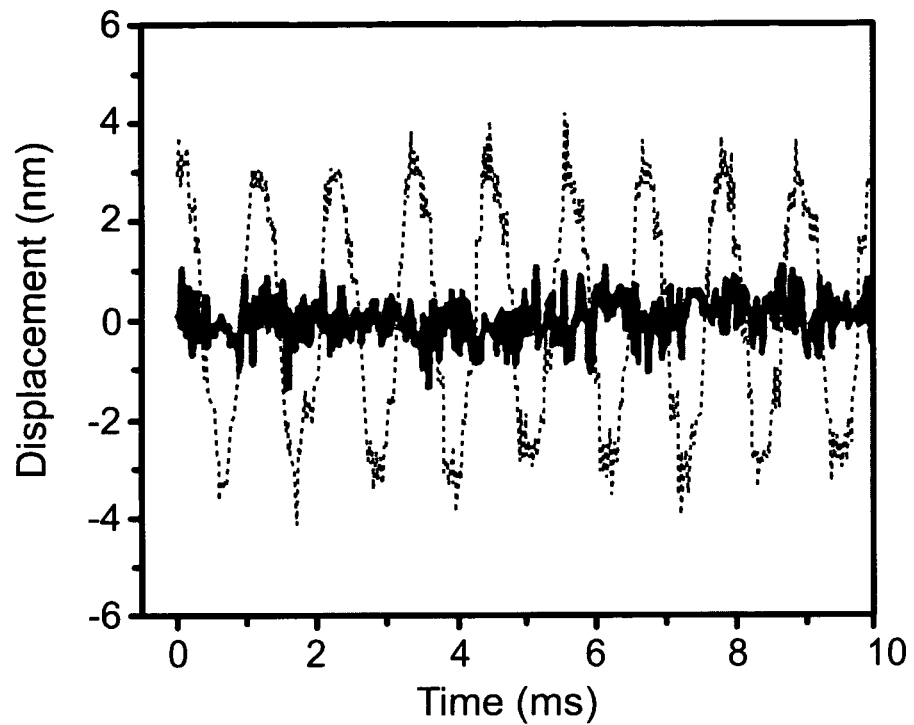
FIG. 5A depicts cantilever deflection caused by cellular movement of BY4741 cells. The dashed line is data recorded for a living cell and the solid line is data for a dead cell.
Figure 5B:
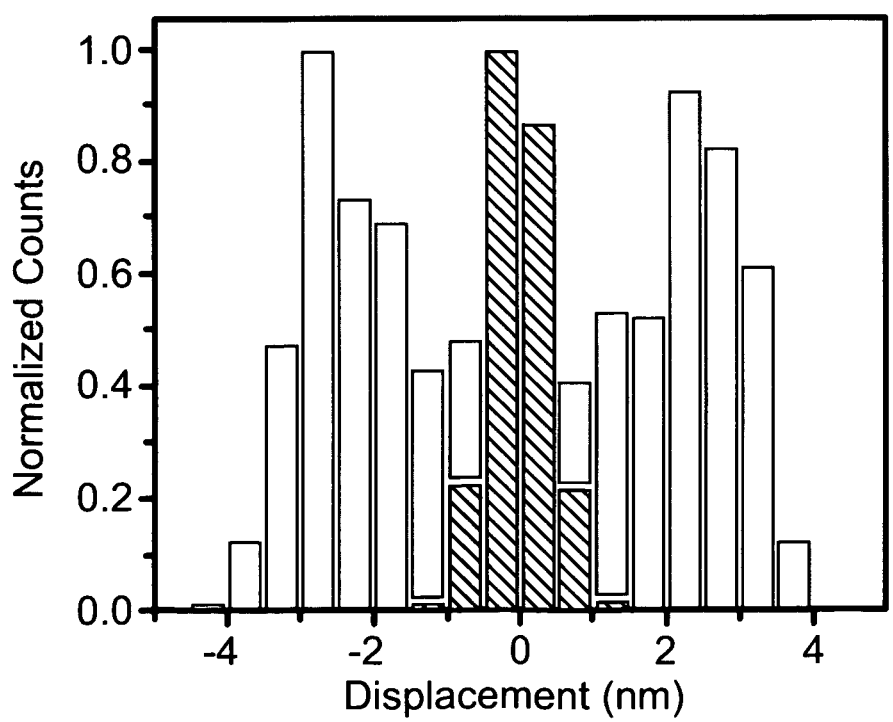
FIG. 5B depicts histograms of cantilever displacement caused by the movement of living cells (open bars) and dead cells (hatched bars).

In FIG. 5A a short section of the cantilever motion as a function of time for a living and dead cell of wild-type BY4741 is shown. Clear differences are discernable in both the nature and amplitude of the motion. Histograms of the cantilever's vertical deflection of living cells clearly demonstrate that the motion is bimodal and oscillatory (FIG. 5B). Gaussian fits to both peaks in the histogram revealed average displacements of 2.87±0.50 nm for the BY4741 cells, 3.87±0.69 nm for the W303.1B cells and 4.12±0.65 nm for the CC304.1 cells. In contrast, dead cells (of all strains) fit well to a single normal/Gaussian distribution with maximum amplitude of 0.75 nm, consistent with random background noise, instrumental noise and/or Brownian motion.

Figure 6A:
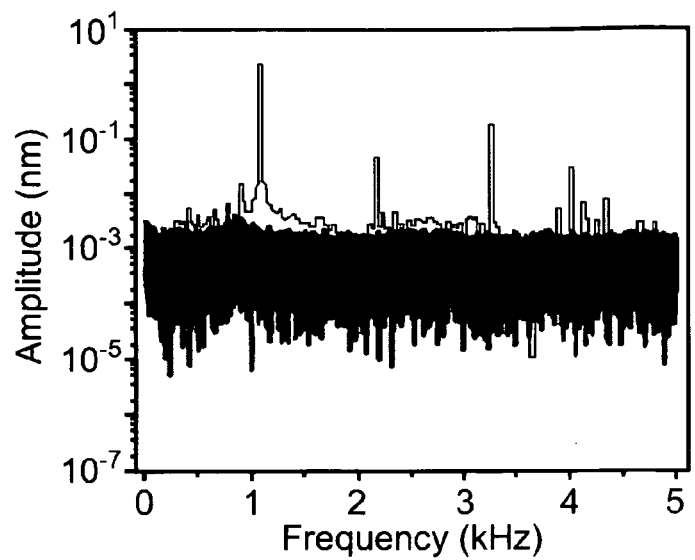
FIGS. 6A-C depicts Fast Fourier Transform (FFT) spectra of the cellular movement for each cell type. Note that the amplitude is plotted on a logarithmic scale. Each FFT spectrum has an almost identical set of peaks. The principal peak is located at $1.088 \pm 0.003$ kHz. The open line is the living cell and the solid (filled) black line is the dead cell. Dead cells always display a broad peak located at 870 Hz, slightly lower in frequency from the principal peak.
Figure 6B:
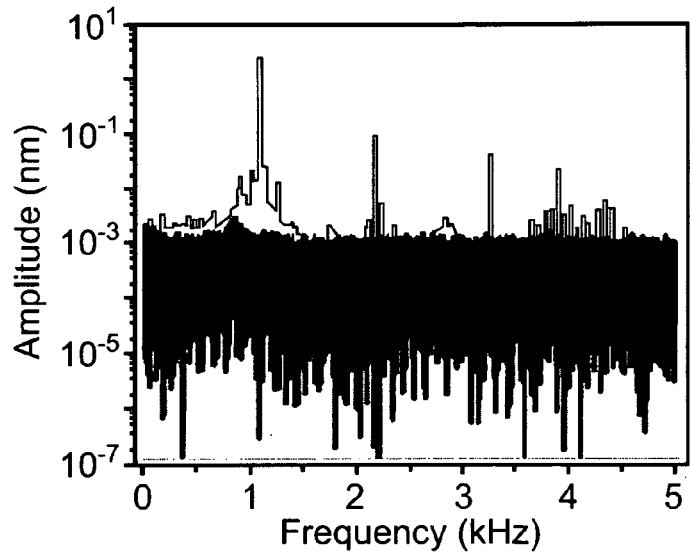
Figure 6C:
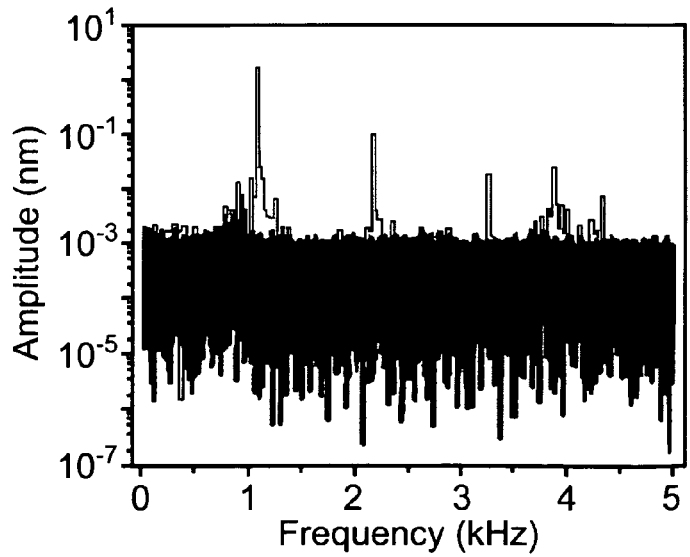

The Fast Fourier Transform (FFT) of the motion of the cell wall versus time enables the frequency characteristics of the cell wall motion to be explored. The FFT of the BY4741 cells (FIG. 6A) consistently displayed a principal peak at 1.088±0.003 kHz with weak overtones, 1-2 orders of magnitude lower at 2.171±0.005 kHz and 3.257±0.006 kHz. A group of peaks also appeared between 3.694±0.068 kHz and 4.363±0.035 kHz. This FFT was reproducible during the course of one experiment, from day to day and with different AFM cantilevers. The data shown is representative of 150 individual experiments carried out over 8 months. The FFTs of dead cells are clearly different and display no significant peaks, except a small broad feature that always appeared at about 870 Hz. This allowed us to clearly distinguish between living and dead cells on an individual basis. This broad feature in the FFT of dead cells may be related to the natural frequency of the cell. W303.1B (FIG. 6B) and CC304.1 (FIG. 6C) also exhibited similar peaks in their FFT when compared to BY4741 cells, suggests a common mechanism producing the observed oscillatory motion.

The observed motion was determined to be solely due to the cell wall motion through an extensive series of control experiments. No resonances were observed for the tip when in contact with a mica or rubber surface (in air and in fluid) up to the measurement limit of 100 kHz. When the AFM tip was free in the air the only peak observed was the natural resonance of the cantilevers, which were 17.265±1.018 kHz (0.06 N/m tip) and 50.484±1.240 kHz for the (0.12 N/m tip).

To ensure that no cellular damage occurred during measurements, the contact force used was always below 12 nN and cells were topographically imaged before and after measurements to confirm that the probe caused no irreversible changes. However, if the contact force was increased in 5 nN steps, distinct changes in the FFT spectrum were only observed when the applied force exceeded 20 nN. Interestingly, these changes depended on cell type. A surface contour plot was constructed by representing the peak intensities using a color lookup table and plotting each FFT as a function of applied force. We increased and decreased the force from 10 nN to 100 nN for each measurement. Each force cycle was repeated three times for each cell and very little hysteresis was observed between each cycle. Each cell type also exhibited a distinct force threshold at which the observed oscillatory motion stops.

Figure 7A:
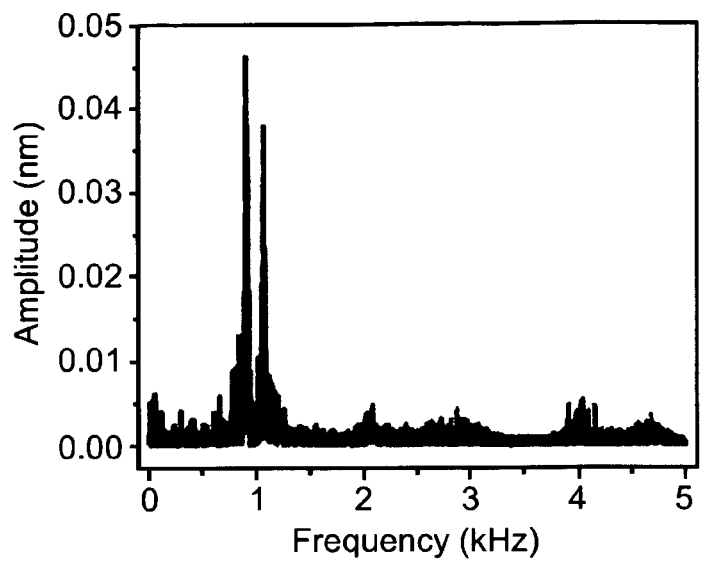
FIGS. 7A-C depict the effect of applied force after the characteristic threshold force is a splitting of the principal peak by about 160 Hz and a marked decrease in amplitude.
Figure 7B:
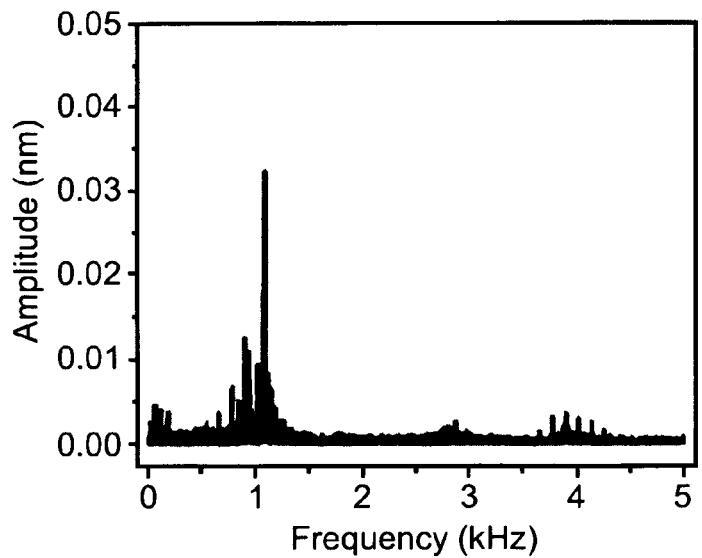
Figure 7C:
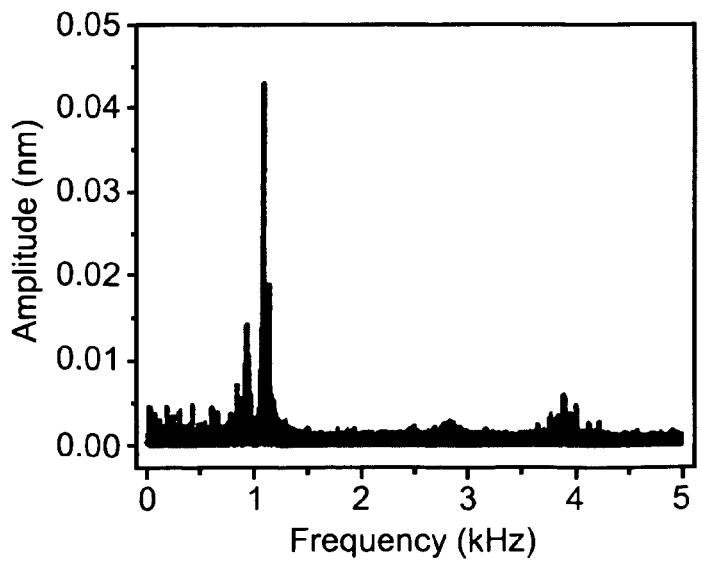

The threshold forces varied according to cell type as follows: 89.51±2.50 nN for the BY4741 cells, 63.66±2.59 nN for the W303.1B cells and 58.49±2.56 nN for the CC304.1 cells. Above the threshold force, the amplitude of the peak at 1.088±0.003 kHz decreased about 3 orders of magnitude and split by about 160 Hz into two asymmetrical peaks centered at 0.992±0.007 kHz. This splitting was observed for all cell types (FIG. 7A-C). On the other hand, the dead cells showed no dependence on contact force and the contour plots are relatively featureless except for the broad feature at 870 Hz that did not demonstrate any force dependence. In general, the amplitude of the principal peak centered at 1.088±0.003 kHz increased until the threshold force was reached after which it decreases to become a minimum for both wild-types BY4741 and W303.1B. Likewise, the principal peak was observed to increase by 30 Hz until higher applied forces at which it moved back to its initial starting position at 1.088±0.003 kHz. For the respiratory-incompetent mutant, CC304.1, the FFTs were significantly more sensitive to force. The peak at 1.088±0.003 kHz was observed to become quite complex at forces above 22 nN. This indicates that the respiratory-incompetent mutant exhibits significantly different nanomechanical behavior at the cell wall. However, after the force threshold was exceeded the principal peak split into two peaks similar to the wild type cells.

Representing the observed cellular movement as .wav files also provided clearly distinguishable sound characteristics to be synthesized of dead, healthy and perturbed cells. The raw data of the cellular movement was easily converted into sound format with commercially available software. Color sonograms were generated using an audio spectral analysis program and they provide a representation of the spectral characteristics of cellular movement with time. The frequencies appear constant with time however the peak centered at 4.2 kHz was observed to fluctuate within 10 Hz. This sonogram is very similar to the other cells but strikingly different from dead cells. Sonograms were also generated for the force cycling experiment. This method of converting the data into audio allowed us to intuitively hear differences in cell motion and the state (living or dead) of a cell. It also provides a convenient visual representation of the cellular motion as a function of time.

Example 2

Use of Quantum Nanomirrors to Determine a Cell Characteristic

Figure 8:
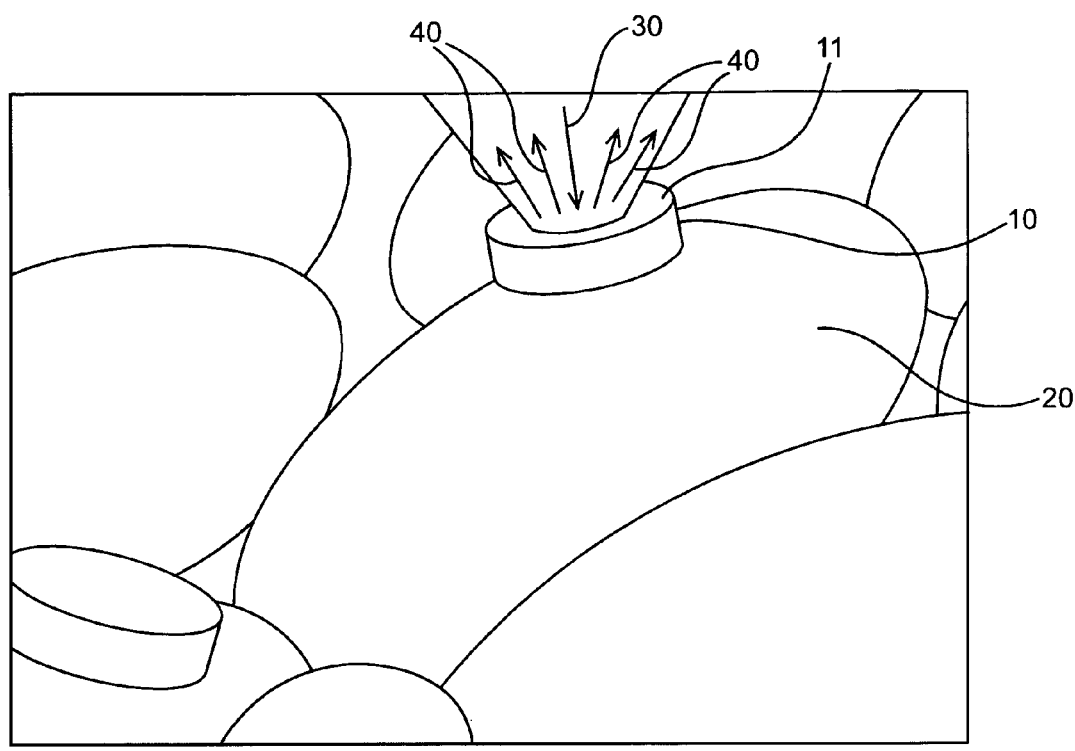
FIG. 8 depicts an exemplary quantum nanomirror attached to a cell surface.

As depicted in FIG. 8, a quantum nanomirror 10 is attached to a cell surface of a cell 20 in a sample. A laser beam (incident beam 30) scans the sample, locates the mirror reflector surface 11 by reflection (reflected beams 40) onto a high resolution CCD array. The laser then follows the motion of the cell membrane through the beam deflection technique in real time. The data recorded are compared to a database using advance neural network analysis such as developed by DARPA for speech recognition. The system can be used to classify and study the effects of small molecules and biological agents; and can also be used for drug development.

Figure 9:
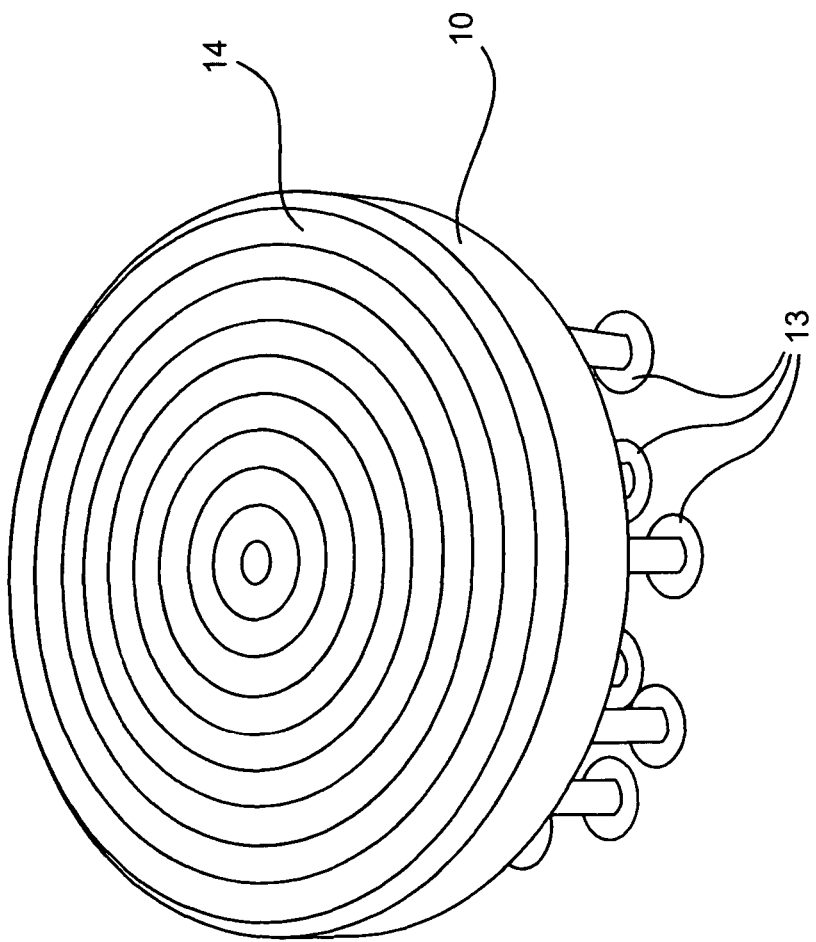
FIG. 9 depicts a top view of an exemplary quantum nanomirror.

FIG. 9 presents a top view of a quantum nanomirror 10. The micron-sized silicon, PDMS, or SiNx disk has an optical grating texture 14 that diffracts light. In FIG. 9, cell attachment moieties 13 are shown, that provide for attachment of the quantum nanomirror to the cell surface. Different disks can be made with different patterns of gratings, e.g., linear, circular (e.g. radial). In addition, the pitch of the gratings can vary. The resulting diffraction pattern, when illuminated by light, serves as a way to identify the individual disks. In addition, the diffraction pattern provides light beams for analyzing the motion of the disk (and hence the cell membrane to which the disk is attached). In another exemplary embodiment, an interdigitated grating has a spiral configuration, where the offset of the grating elements provides an indication of cell membrane movement through the offset of adjacent diffractive grooves. See, e.g., Manalis et al. (1996) *Appl. Phys. Lett.* 69:3944.

Figure 10:
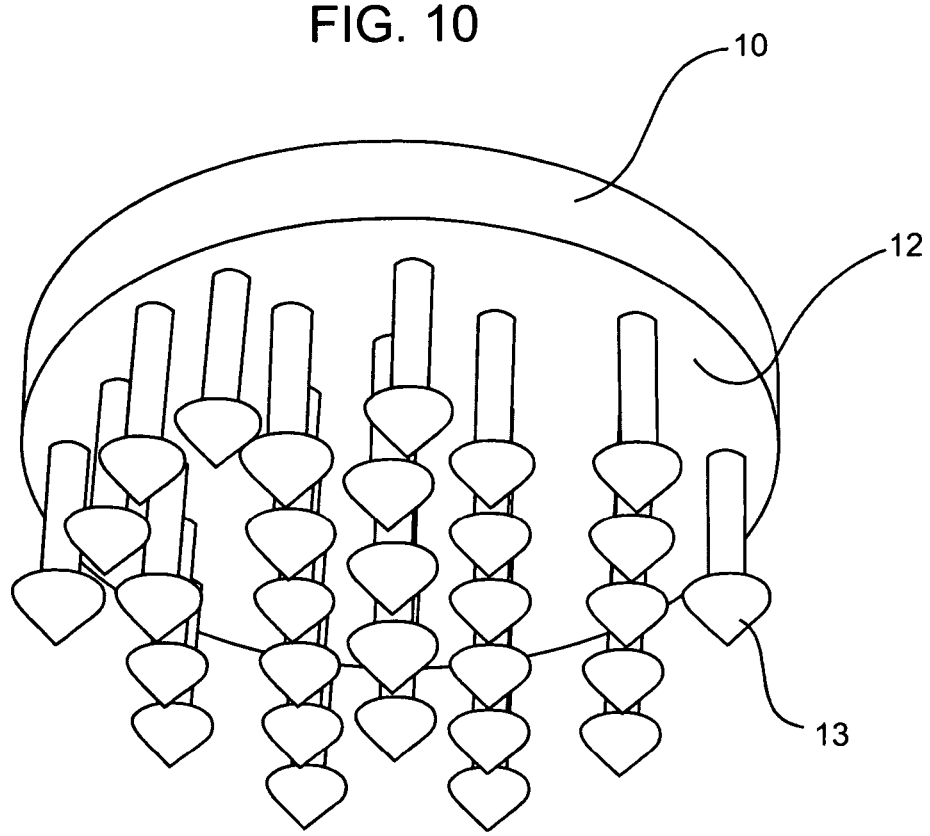
FIG. 10 depicts a bottom view of an exemplary quantum nanomirror.

FIG. 10 depicts the attachment surface of a quantum nanomirror 10, where the cell attachment surface 12 contains an immunobilized or self-assembled array of biomolecules (cell attachment moieties 13) to target specific cells. Examples of specific molecules (attachment moieties) include viral proteins, antibodies, receptor ligands, antibodies specific for cell surface receptors, receptor agonists, receptor antagonists, lectins, etc. The biocoating (attachment moieties) can be detected by coding the attachment moieties with the appropriate grating on the reflector surface. Thus, the identity of the attachment moieties can be coded by the pattern and/or pitch of the diffraction grating.

Figure 11:
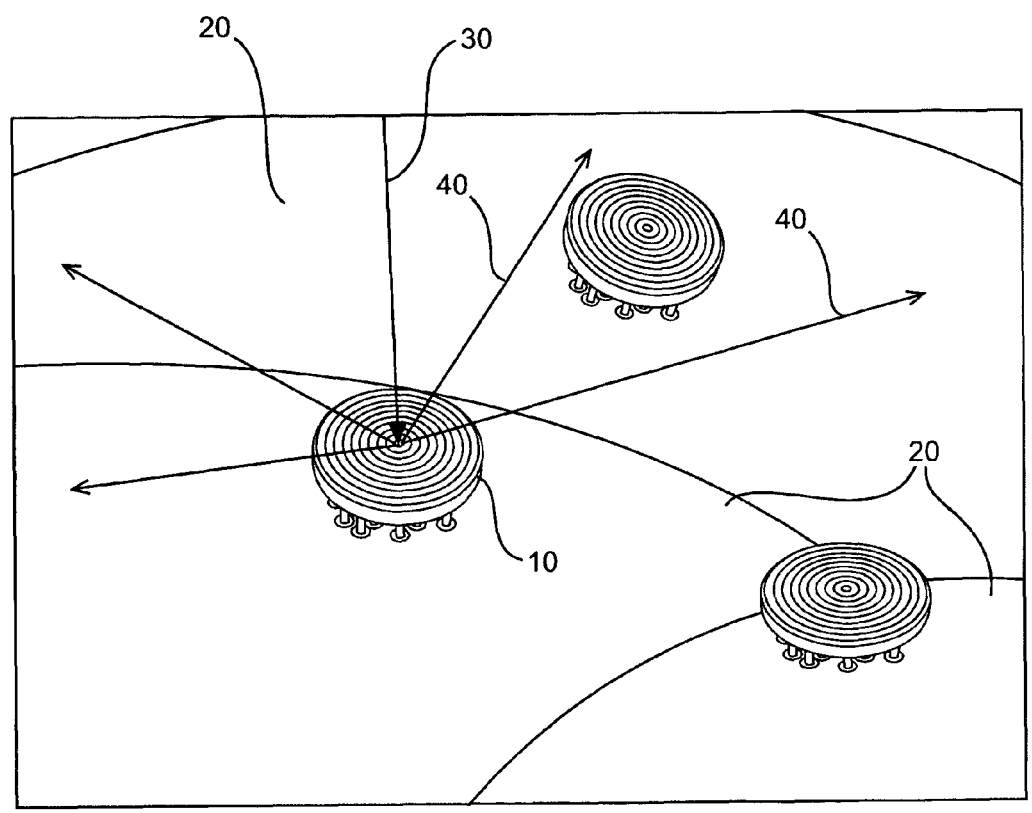
FIG. 11 depicts an exemplary quantum nanomirror attached to a cell surface in liquid medium.

FIG. 11 provides a schematic representation of a diffractive quantum nanomirror 10 on the surface of a cell 20. The laser beam incident on the disk (incident light beam 30) is diffracted (reflected light 40), and the diffracted light is detected by a high resolution CCD array and identified, to detect the motion of the cell. The addition of an external stimulus, e.g., an agonist, an inhibitor, or other biochemical agent is tracked by monitoring the motion of the diffraction spots. In addition, a biochemical agent immobilized on the attachment surface of the disk can provide an external stimulus, and the response of the cell to the stimulus detected by monitoring the motion of the diffraction spots.

As one example, the effect of a drug such as a taxane (e.g., Taxol) can be studied at a single cell level, even in the presence of other tissues. Other applications of the technique include monitoring of cancer cells; the use of a second photon beam to specifically release a second small molecule agent for rapid automated drug screening; and the use of biodegradable mirrors.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A micromirror consisting of:
a flat member, the flat member having a reflector surface and a cell attachment surface, wherein the reflector surface and the cell attachment surface are on opposite faces of the flat member of the micromirror; and
one or more cell attachment moieties immobilized on the cell attachment surface, wherein the reflector surface of the micromirror is movably responsive to movements of an attached cell, and wherein the surface area of the micromirror is in a range from 25 nm$^2$ to about 750 nm$^2$.

2. The micromirror of claim 1, wherein the reflector surface comprises a diffraction grating.

3. The micromirror of claim 1, wherein each of the one or more cell attachment moieties is selected from an antibody, a polypeptide, an integrin, a virus attachment protein, a carbohydrate, and a ligand for a cell surface receptor.

4. The micromirror of claim 1, wherein the reflector surface comprises silicon dioxide, polydimethylsiloxane, or silicon nitride.

5. The micromirror of claim 1, wherein the cell attachment surface comprises from 10 to $10^{10}$ cell attachment moieties immobilized thereon.

6. The micromirror of claim 1, wherein the cell attachment surface comprises 2 or more different cell attachment moieties.

7. An array comprising a plurality of the micromirror of claim 1.

8. The array of claim 7, wherein the array is a two-dimensional array.

9. A micromirror consisting of:
a flat member, the flat member having a reflector surface and a cell attachment surface, wherein the reflector surface and the cell attachment surface are on opposite faces of the flat member of the micromirror; and
one or more cell attachment moieties immobilized on the cell attachment surface, wherein the reflector surface of the micromirror is movably responsive to movements of an attached cell, and wherein the micromirror is circular in shape and has a diameter in a range from 10 nm to 5 µm.

10. The micromirror of claim 9, wherein the reflector surface comprises a diffraction grating.

11. The micromirror of claim 9, wherein each of the one or more cell attachment moieties is selected from an antibody, a polypeptide, an integrin, a virus attachment protein, a carbohydrate, and a ligand for a cell surface receptor.

12. The micromirror of claim 9, wherein the reflector surface comprises silicon dioxide, polydimethylsiloxane, or silicon nitride.

13. The micromirror of claim 9, wherein the cell attachment surface comprises from 10 to $10^{10}$ cell attachment moieties immobilized thereon.

14. The micromirror of claim 9, wherein the cell attachment surface comprises 2 or more different cell attachment moieties.

15. An array comprising a plurality of the micromirror of claim 9.

16. The array of claim 15, wherein the array is a two-dimensional array.

* * * * *